United States Patent
Fine et al.

(10) Patent No.: US 9,989,750 B2
(45) Date of Patent: Jun. 5, 2018

(54) SAMPLE PROCESSING IMPROVEMENTS FOR MICROSCOPY

(71) Applicant: Alentic Microscience Inc., Halifax (CA)

(72) Inventors: Alan Marc Fine, Prospect (CA); Hershel Macaulay, Bedford (CA); Noah Hymes-Vandermeulen, Halifax (CA)

(73) Assignee: Alentic Microscience Inc., Halifax, Nova Scotia (CA)

( * ) Notice: Subject to any disclaimer, the term of this patent is extended or adjusted under 35 U.S.C. 154(b) by 0 days. days.

(21) Appl. No.: 15/360,724

(22) Filed: Nov. 23, 2016

(65) Prior Publication Data

US 2017/0075099 A1    Mar. 16, 2017

Related U.S. Application Data

(62) Division of application No. 14/314,743, filed on Jun. 25, 2014, now Pat. No. 9,518,920.
(Continued)

(51) Int. Cl.
*G02B 21/34* (2006.01)
*G01N 21/59* (2006.01)
(Continued)

(52) U.S. Cl.
CPC .............. *G02B 21/34* (2013.01); *G01N 1/28* (2013.01); *G01N 1/4077* (2013.01);
(Continued)

(58) Field of Classification Search
CPC ........... G01N 21/01; G01N 1/00; G02B 21/34
(Continued)

(56) References Cited

U.S. PATENT DOCUMENTS 3,447,863 A    6/1969  Patterson
3,551,023 A *  12/1970 Brackett .............. G06K 19/022
                                                        156/60

(Continued)

FOREIGN PATENT DOCUMENTS

CN    102713720 A    10/2012
CN    105765440      7/2016
(Continued)

OTHER PUBLICATIONS

International Search Report and Written Opinion from corresponding PCT application No. PCT/US2010/054240 mailed Dec. 27, 2010 (16 pages).
(Continued)

Primary Examiner — Roy M Punnoose
(74) Attorney, Agent, or Firm — Fish & Richardson P.C.

(57) ABSTRACT

Among other things, a first surface is configured to receive a sample and is to be used in a microscopy device. There is a second surface to be moved into a predefined position relative to the first surface to form a sample space that is between the first surface and the second surface and contains at least part of the sample. There is a mechanism configured to move the second surface from an initial position into the predefined position to form the sample space. When the sample is in place on the first surface, the motion of the second surface includes a trajectory that is not solely a linear motion of the second surface towards the first surface.

19 Claims, 11 Drawing Sheets

Related U.S. Application Data

(60) Provisional application No. 61/839,735, filed on Jun. 26, 2013.

(51) Int. Cl.

| | | |
|---|---|---|
| *G01N 1/40* | (2006.01) | |
| *G01N 1/28* | (2006.01) | |
| *G01N 15/14* | (2006.01) | |
| *G01N 33/49* | (2006.01) | |
| G01N 35/00 | (2006.01) | |
| G01N 15/00 | (2006.01) | |
| G01N 15/06 | (2006.01) | |
| G01N 15/10 | (2006.01) | |

(52) U.S. Cl.
CPC ......... *G01N 15/1468* (2013.01); *G01N 21/59* (2013.01); *G01N 33/49* (2013.01); *G01N 15/0606* (2013.01); *G01N 35/00029* (2013.01); *G01N 2015/008* (2013.01); *G01N 2015/1087* (2013.01); *G01N 2015/1486* (2013.01)

(58) Field of Classification Search
USPC .................................. 356/244, 36
See application file for complete search history.

(56) References Cited

U.S. PATENT DOCUMENTS

| | | | |
|---|---|---|---|
| 4,338,024 A | 7/1982 | Bolz et al. | |
| 4,612,614 A | 9/1986 | Deindoerfer et al. | |
| 4,682,887 A * | 7/1987 | Bellhouse | G01N 21/51 356/39 |
| 4,744,643 A * | 5/1988 | Taylor | G02B 21/34 356/244 |
| 4,758,083 A * | 7/1988 | Bellhouse | A61J 1/10 356/244 |
| 4,882,284 A | 11/1989 | Kirchanski et al. | |
| 4,950,455 A | 8/1990 | Smith | |
| 4,963,498 A | 10/1990 | Hillman et al. | |
| 5,218,211 A | 6/1993 | Cresswell et al. | |
| 5,307,161 A | 4/1994 | Miyamoto | |
| 5,365,114 A | 11/1994 | Tsurushima et al. | |
| 5,389,779 A | 2/1995 | Betzig et al. | |
| 5,464,752 A | 11/1995 | Kortright et al. | |
| 5,605,813 A * | 2/1997 | Stevens | C12M 23/08 356/244 |
| 5,627,041 A | 5/1997 | Shartle | |
| 5,633,972 A | 5/1997 | Walt et al. | |
| 5,653,939 A | 8/1997 | Hollis et al. | |
| 5,739,527 A | 4/1998 | Hecht et al. | |
| 5,851,489 A | 12/1998 | Wolf et al. | |
| 5,880,830 A | 3/1999 | Schechter | |
| 5,894,349 A | 4/1999 | Harris et al. | |
| 5,932,428 A | 8/1999 | Dubrow et al. | |
| 6,083,763 A | 7/2000 | Balch | |
| 6,104,495 A | 8/2000 | Sieben et al. | |
| 6,180,314 B1 | 1/2001 | Berndt | |
| 6,259,104 B1 | 7/2001 | Baer | |
| 6,280,586 B1 | 8/2001 | Wolf et al. | |
| 6,297,025 B1 | 10/2001 | Sugihara et al. | |
| 6,302,985 B1 | 10/2001 | Takahashi et al. | |
| 6,312,960 B1 | 11/2001 | Balch et al. | |
| 6,323,944 B1 | 11/2001 | Xiao | |
| 6,387,707 B1 | 5/2002 | Seul et al. | |
| 6,396,980 B1 | 5/2002 | Liu et al. | |
| 6,411,434 B1 * | 6/2002 | Eastman | B01L 3/508 356/246 |
| 6,432,720 B2 | 8/2002 | Chow | |
| 6,506,664 B1 | 1/2003 | Beyne et al. | |
| 6,621,079 B1 | 9/2003 | Shao | |
| 6,690,464 B1 | 2/2004 | Lewis et al. | |
| 6,723,290 B2 | 4/2004 | Wardlaw | |
| 6,773,676 B2 * | 8/2004 | Schembri | B01L 3/508 422/559 |
| 6,784,982 B1 | 8/2004 | Blumenfeld et al. | |
| 6,803,238 B1 | 10/2004 | Eggers | |
| 6,844,150 B2 | 1/2005 | Weiss et al. | |
| 6,867,851 B2 | 3/2005 | Blumenfeld et al. | |
| 6,901,086 B2 | 5/2005 | Li | |
| 7,009,172 B2 | 3/2006 | Publicover et al. | |
| 7,023,563 B2 | 4/2006 | Li | |
| 7,079,256 B2 | 7/2006 | Li | |
| 7,142,571 B2 | 11/2006 | Li | |
| 7,151,246 B2 | 12/2006 | Fein et al. | |
| 7,153,720 B2 | 12/2006 | Augusto | |
| 7,280,222 B2 | 10/2007 | Li | |
| 7,310,151 B2 | 12/2007 | Li | |
| 7,326,930 B2 | 2/2008 | Crawely | |
| 7,385,175 B2 | 6/2008 | Li et al. | |
| 7,423,766 B1 | 9/2008 | Li | |
| 7,425,460 B2 | 9/2008 | Pain | |
| 7,443,507 B2 | 10/2008 | Ran | |
| 7,466,409 B2 | 12/2008 | Scherer et al. | |
| 7,476,787 B2 | 1/2009 | Thomas et al. | |
| 7,518,731 B2 | 4/2009 | Li | |
| 7,524,459 B2 | 4/2009 | Adams et al. | |
| 7,626,695 B2 | 12/2009 | Betzig et al. | |
| 7,651,598 B2 | 1/2010 | Shapiro et al. | |
| 7,693,571 B2 | 4/2010 | Arnone et al. | |
| 7,719,685 B2 | 5/2010 | Li | |
| 7,727,752 B2 | 6/2010 | Klink et al. | |
| 7,738,945 B2 | 6/2010 | Fauver et al. | |
| 7,751,048 B2 | 7/2010 | Yang et al. | |
| 7,773,227 B2 | 8/2010 | Yang et al. | |
| 7,792,246 B2 | 9/2010 | Rodenburg et al. | |
| 7,796,797 B2 | 9/2010 | Nakaya et al. | |
| 7,850,916 B2 | 12/2010 | Wardlaw | |
| 7,936,501 B2 | 5/2011 | Smith et al. | |
| 7,982,883 B2 | 7/2011 | Cui et al. | |
| 7,990,539 B2 | 8/2011 | Li | |
| 8,004,692 B2 | 8/2011 | Li | |
| 8,027,083 B2 | 9/2011 | Smith et al. | |
| 8,089,630 B2 | 1/2012 | Davis et al. | |
| 8,120,783 B2 | 2/2012 | Li | |
| 8,314,933 B2 | 11/2012 | Cui | |
| 8,345,227 B2 | 1/2013 | Zahniser et al. | |
| 8,446,667 B2 | 5/2013 | Smith et al. | |
| 8,456,633 B2 | 6/2013 | Lewis et al. | |
| 8,477,294 B2 | 7/2013 | Zahniser et al. | |
| 8,488,111 B2 | 7/2013 | Zahniser et al. | |
| 8,506,909 B2 * | 8/2013 | Sunwoldt | B82Y 35/00 219/201 |
| 9,041,790 B2 | 5/2015 | Fine | |
| 9,075,225 B2 | 7/2015 | Fine | |
| 9,133,507 B2 * | 9/2015 | Testa | B01L 3/508 |
| 9,518,920 B2 * | 12/2016 | Fine | G02B 21/34 |
| 2001/0046702 A1 * | 11/2001 | Schembri | B01L 3/508 435/287.2 |
| 2001/0052930 A1 | 12/2001 | Adair | |
| 2002/0147384 A1 | 10/2002 | Uchikubo | |
| 2004/0171076 A1 | 9/2004 | Dejneka | |
| 2005/0048498 A1 | 3/2005 | Woudenberg et al. | |
| 2005/0190286 A1 * | 9/2005 | Kaduchak | G01N 15/1475 348/370 |
| 2005/0271548 A1 | 12/2005 | Yang et al. | |
| 2006/0223165 A1 | 10/2006 | Chang et al. | |
| 2006/0263888 A1 | 11/2006 | Fritz et al. | |
| 2007/0087442 A1 | 4/2007 | Wardlaw | |
| 2007/0207061 A1 | 9/2007 | Yang et al. | |
| 2007/0243117 A1 | 10/2007 | Wardlaw | |
| 2007/0258096 A1 | 11/2007 | Cui et al. | |
| 2008/0095312 A1 | 4/2008 | Rodenburg et al. | |
| 2008/0144899 A1 | 6/2008 | Varma et al. | |
| 2008/0194012 A1 | 8/2008 | Lee | |
| 2008/0259443 A1 | 10/2008 | Smith et al. | |
| 2008/0259444 A1 | 10/2008 | Smith | |
| 2008/0285040 A1 | 11/2008 | Fourkas et al. | |
| 2008/0319298 A1 | 12/2008 | Huys | |
| 2009/0072332 A1 | 3/2009 | Dekker | |
| 2009/0093970 A1 | 4/2009 | Lewy | |
| 2009/0163432 A1 | 6/2009 | Takamatsu et al. | |
| 2009/0174936 A1 | 7/2009 | Olszak | |
| 2009/0220125 A1 | 9/2009 | Ren et al. | |

(56) References Cited

U.S. PATENT DOCUMENTS

| | | |
|---|---|---|
| 2009/0225319 A1 | 9/2009 | Lee et al. |
| 2009/0233329 A1 | 9/2009 | Rodriguez et al. |
| 2010/0033561 A1 | 2/2010 | Hersee |
| 2010/0067827 A1 | 3/2010 | Ozcan et al. |
| 2010/0097599 A1 | 4/2010 | Lewis et al. |
| 2010/0248300 A1 | 9/2010 | Yoshida et al. |
| 2010/0290049 A1 | 11/2010 | Yang et al. |
| 2010/0296094 A1 | 11/2010 | Yang et al. |
| 2011/0001460 A1 | 1/2011 | Steinmetzer |
| 2011/0037846 A1 | 2/2011 | Huang |
| 2011/0070606 A1 | 3/2011 | Winkelman et al. |
| 2011/0096157 A1 | 4/2011 | Fine et al. |
| 2011/0149280 A1* | 6/2011 | Juhl .................. G01N 21/0303 356/319 |
| 2011/0151502 A1 | 6/2011 | Kendall et al. |
| 2011/0181884 A1 | 7/2011 | Cui et al. |
| 2011/0211058 A1 | 9/2011 | McCollum et al. |
| 2011/0234757 A1 | 9/2011 | Zheng et al. |
| 2011/0249109 A1 | 10/2011 | Fine |
| 2011/0254533 A1 | 10/2011 | Gong |
| 2012/0223217 A1 | 9/2012 | Zheng et al. |
| 2012/0223291 A1 | 9/2012 | Klem et al. |
| 2012/0224053 A1 | 9/2012 | Vykoukal |
| 2013/0002847 A1 | 1/2013 | Zahniser et al. |
| 2013/0052331 A1 | 2/2013 | Kram et al. |
| 2013/0217065 A1* | 8/2013 | Neef .................. G01N 1/2813 435/40.5 |
| 2014/0002662 A1 | 1/2014 | Lewis et al. |
| 2014/0152801 A1 | 6/2014 | Fine et al. |
| 2015/0002834 A1 | 1/2015 | Fine et al. |
| 2015/0241679 A1 | 8/2015 | Fine et al. |
| 2016/0041200 A1 | 2/2016 | Fine |
| 2016/0187235 A1 | 6/2016 | Fine et al. |
| 2016/0356999 A1 | 12/2016 | Fine |
| 2017/0322402 A1 | 11/2017 | Fine et al. |

FOREIGN PATENT DOCUMENTS

| | | |
|---|---|---|
| CN | 105974571 A | 9/2016 |
| DE | 102011117228 | 5/2013 |
| EP | 0170565 | 2/1986 |
| EP | 1756260 | 2/2007 |
| EP | 2012114 | 1/2009 |
| EP | 2330215 A1 | 6/2011 |
| EP | 2494400 | 9/2012 |
| EP | 2554987 A1 | 2/2013 |
| EP | 2954310 | 12/2015 |
| EP | 3014330 | 5/2016 |
| EP | 3268737 | 1/2018 |
| JP | S58-182267 | 10/1983 |
| JP | S62-262001 | 11/1987 |
| JP | S63-229426 | 9/1988 |
| JP | S64-71172 | 3/1989 |
| JP | 4-316478 | 11/1992 |
| JP | 5-219937 | 8/1993 |
| JP | 5243790 | 9/1993 |
| JP | H09-021963 | 1/1997 |
| JP | 11-64215 | 3/1999 |
| JP | 2000-146910 | 5/2000 |
| JP | 2001-78175 | 3/2001 |
| JP | 2002-525587 | 8/2002 |
| JP | 2006-003653 | 1/2006 |
| JP | 2008-501999 | 1/2008 |
| JP | 2008-192813 | 8/2008 |
| JP | 2009-65178 | 3/2009 |
| JP | 5059882 | 10/2012 |
| JP | 2013-507630 | 3/2013 |
| JP | 2013-509618 | 3/2013 |
| JP | 2015-215624 | 12/2015 |
| WO | WO2000/012123 | 3/2000 |
| WO | WO2005/121749 | 12/2005 |
| WO | WO2008/112416 | 9/2008 |
| WO | WO 2006/133360 | 9/2009 |
| WO | WO2009/111573 | 9/2009 |
| WO | WO2009/111577 | 9/2009 |
| WO | WO 2010/148252 | 12/2010 |
| WO | WO2011/053631 | 5/2011 |
| WO | WO 2012/094523 | 7/2012 |
| WO | WO 2014/121388 | 5/2013 |
| WO | WO2014/205576 | 12/2014 |
| WO | WO2016/141487 | 9/2016 |

OTHER PUBLICATIONS

Ji, Honghao, et al., "Contact Imaging: Stimulation and Experiment", IEEE Transactions on Circuits and Systems—I: Regular Papers, vol. 54, No. 8, Aug. 2007 (13 pages).

Bayer, Manfred E. and John L. Sloyer, Jr., "The electrophoretic mobility of Gram-negative and Gram-positive bacteria: an electrokinetic analysis", Jan. 31, 1990 (8 pages).

Cook, G.M.W., "Glycoproteins in Membranes", Biol. Rev. (1968) 43, pp. 363-391, Jan. 1968 (29 pages).

Kiuchi, Masato and Akiyoshi Chayahara, "Titanium nitride for transparent conductors", Appl. Phys. Lett. 64(8), Feb. 21, 1994 (3 pages).

Alpha MED Scientific, Inc., "MED64: A low-noise multi-electrode array system for in vitro extracellular electrophysiology", MED64 product information, www.med64.com, received Jan. 31, 2012 (16 pages).

OmniVision, "The World's First 1/4 —inch 5-Megapixel SoC Image Sensor with OmniBSI™ Technology", OV5642, version 1.1, Dec. 2009 (2 pages).

International Preliminary Report on Patentability from corresponding PCT application No. PCT/US2010/054240 mailed May 10, 2012 (7 pages).

European Communication for EP application No. 10827423.4 issued Jun. 6, 2012 (2 pages).

Zheng, et al., "Supporting Information", SI Text, www.pnas.org/cgi/doi/10.1073/pnas.1110681108, 2011, 3 pages.

Adams ML, Enzelberger M, Quake S, Scherer A. Microfluidic integration on detector arrays for absorption and fluorescence micro-spectrometers. Sensors and Actuators A: Physical. 2003;104(1):25-31. doi: 10.1016/S0924-4247(02)00477-6.

Adams M, DeRose G, Quake SR, Scherer A. Fundamental approach for optoelectronic and microfluidic integration for miniaturizing spectroscopic devices. . 2002:1-6. doi: 10.1117/12.469818.

Alkaisi MM, Blaikie RJ, McNab SJ, Cheung R, Cumming DRS. Sub-diffraction-limited patterning using evanescent near-field optical lithography. Appl Phys Lett. 1999;75(22):3560-3562. http://dx.doi.org/10.1063/1.125388. doi: 10.1063/1.125388.

Allier CP, Hiernard G, Poher V, Dinten JM. Bacteria detection with thin wetting film lensless imaging. Biomed Opt Express. 2010;1(3):762-770. doi: 10.1364/BOE.1.000762.

Beese L, Feder R, Sayre D. Contact x-ray microscopy. A new technique for imaging cellular fine structure. Biophys J. 1986;49(1):259-268. doi: 10.1016/S0006-3495(86)83639-6.

Beiderman M, Tam T, Fish A, Jullien GA, Yadid-Pecht O. A low-light CMOS contact imager with an emission filter for biosensing applications. Biomedical Circuits and Systems, IEEE Transactions on. 2008;2(3):193-203. doi: 10.1109/TBCAS.2008.2001866.

Bishara W, Su T, Coskun AF, Ozcan A. Lensfree on-chip microscopy over a wide field-of-view using pixel super-resolution. Opt Express. 2010;18(11):11181-11191. http://www.opticsexpress.org/abstract.cfm?URI=oe-18-11-11181.

Coskun AF, Sencan I, Su T, Ozcan A. Lensless wide-field fluorescent imaging on a chip using compressive decoding of sparse objects. Opt Express. 2010;18(10):10510-10523. http://www.opticsexpress.org/abstract.cfm?URI=oe-18-10-10510.

Cui X, Lee LM, Heng X, et al. Lensless high-resolution on-chip optofluidic microscopes for caenorhabditis elegans and cell imaging. Proceedings of the National Academy of Sciences. 2008. doi: 10.1073/pnas.0804612105.

D.C. Ng, Nakagawa T, Mizuno T, et al. Integrated in vivo neural imaging and interface CMOS devices: Design, packaging, and implementation. IEEE Sens J. 2008;8(1):121-130. http://pubget.com/paper/pgtmp_3c74d9653c84d6253dff533a781220fb. doi: 10.1109/JSEN.2007.912921.

(56) References Cited

OTHER PUBLICATIONS

Dattner Y, Yadid-Pecht O. Low light CMOS contact imager with an integrated poly-acrylic emission filter for fluorescence detection. Sensors (Basel). 2010;10(5):5014-5027. doi: 10.3390/s100505014; 10.3390/s100505014.

Eggers, M. et al, "A Microchip for Quantitative Detection of Molecules Utilizing Luminescent and Radioisotope Reporter Groups", 516 BioFeature, vol. 17, No. 3, 1994 (8 pages).

Faulkner HML, Rodenburg JM. Movable aperture lensless transmission microscopy: A novel phase retrieval algorithm. Phys Rev Lett. 2004;93(2):023903. http://link.aps.org/doi/10.1103/PhysRevLett.93.023903.

Feder R, Costa JL, Chaudhari P, Sayre D. Improved detail in biological soft X-ray microscopy: Study of blood platelets. Science. 1981;212(4501):1398-1400.

Fischer UC, Zingsheim HP. Submicroscopic contact imaging with visible light by energy transfer. Applied Physics Letters. 1982;40(3):195-197. doi: 10.1063/1.93050.

Greenbaum A, Luo W, Su TW, et al. Imaging without lenses: Achievements and remaining challenges of wide-field on-chip microscopy. Nat Methods. 2012;9(9):889-895. doi: 10.1038/nmeth.2114; 10.1038/nmeth.2114.

Gurkan U, Moon S, Geckil H, et al. Miniaturized lensless imaging systems for cell and microorganism visualization in point-of-care testing. Biotechnol J. 2011;6(2):138-149. http://europepmc.org/abstract/MED/21298800.

Heng X, Erickson D, Baugh LR, et al. Optofluidic microscopy-a method for implementing a high resolution optical microscope on a chip. Lab Chip. 2006;6(10):1274-1276. http://dx.doi.org/10.1039/B604676B. doi: 10.1039/B604676B.

Heng X, Erickson D, Psaltis D, Yang C. A new imaging method: Optofluidic microscopy. . 2005:60030F-60030F. doi: 10.1117/12.632157.

Heng X, Hsiao E, Psaltis D, Yang C. An optical tweezer actuated, nanoaperture-grid based optofluidic microscope implementation method. Opt Express. 2007;15(25):16367-16375. http://www.opticsexpress.org/abstract.cfm?URI=oe-15-25-16367.

Ji, Honghao, Abshire PA, Urdaneta M, Smela E. CMOS contact imager for monitoring cultured cells. Circuits and Systems, 2005 ISCAS 2005 IEEE International Symposium on. 2005:3491-3494 vol. 4. doi: 10.1109/ISCAS.2005.1465381.

Ji, Honghao, Sander D, Haas A, Abshire PA. A CMOS contact imager for locating individual cells. Circuits and Systems, 2006 ISCAS 2006 Proceedings 2006 IEEE International Symposium on. 2006:4 pp. doi: 10.1109/ISCAS.2006.1693345.

Ji, Honghao, Sander D, Haas A, Abshire PA. Contact imaging: Simulation and experiment. Circuits and Systems I: Regular Papers, IEEE Transactions on. 2007;54(8):1698-1710. doi: 10.1109/TCSI.2007.902409.

Isikman SO, Bishara W, Mavandadi S, et al. Lens-free optical tomographic microscope with a large imaging volume on a chip. Proceedings of the National Academy of Sciences. 2011. doi: 10.1073/pnas.1015638108.

Isikman SO, Sencan I, Mudanyali O, Bishara W, Oztoprak C, Ozcan A. Color and monochrome lensless on-chip imaging of caenorhabditis elegans over a wide field-of-view. Lab Chip. 2010;10(9):11094112. http://dx.doi.org/10.1039/C001200A. doi: 10.1039/C001200A.

Kobayashi T, Tamura H, Hatanaka Y, et al. Functional neuroimaging by using an implantable CMOS multimodal device in a freely-moving mouse. Biomedical Circuits and Systems Conference (BioCAS), 2011 IEEE. 2011:110-113. doi: 10.1109/BioCAS.2011.6107739.

Lange D, Storment CW, Conley CA, Kovacs GTA. A microfluidic shadow imaging system for the study of the nematode caenorhabditis elegans in space. Sensors Actuators B: Chem. 2005;107(2):904-914. doi: 10.1016/j.snb.2004.12.039.

Lee L, Cui X, Yang C. The application of on-chip optofluidic microscopy for imaging giardia lamblia trophozoites and cysts. Biomed Microdevices. 2009;11(5):951-958. http://dx.doi.org/10.1007/s10544-009-9312-x. doi: 10.1007/s10544-009-9312-x.

Lee M, Yaglidere O, Ozcan A. Field-portable reflection and transmission microscopy based on lensless holography. Biomed Opt Express. 2011;2(9):2721-2730. doi: 10.1364/BOE.2.002721; 10.1364/BOE.2.002721.

Lee SA, Zheng G, Mukherjee N, Yang C. On-chip continuous monitoring of motile microorganisms on an ePetri platform. Lab Chip. 2012;12(13):2385-2390. doi: 10.1039/c21c40090a; 10.1039/c21c40090a.

Lorenz Ks, Salama P, Dunn KW, Delp EJ. Digital correction of motion artefacts in microscopy image sequences collected from living animals using rigid and nonrigid registration. J Microsc. 2012; 245(2):148-160. doi: 10.1111/j.1365-2818.2011.03557.x; 2012.

Maiden AM, Rodenburg JM. An improved ptychographical phase retrieval algorithm for diffractive imaging. Ultramicroscopy. 2009;109(10):1256-1262. doi: 10.1016/j.ultramic.2009.05.012.

Maiden AM, Rodenburg JM, Humphry MJ. Optical ptychography: A practical implementation with useful resolution. Opt Lett. 2010;35(15):2585-2587. http://ol.osa.org/abstract.cfm?URI=ol-35-15-2585.

Manaresi N, Romani A, Medoro G, et al. A CMOS chip for individual cell manipulation and detection. Solid-State Circuits, IEEE Journal of. 2003;38(12):2297-2305. doi: 10.1109/JSSC.2003.819171.

McCorkle R, Angilello J. Coleman G. Feder R. LA Placa SJ. Flash X-ray microscopy. Science. 1979;205(4404):401-402. doi: 10.1126/science.205.4404.401.

Milanfar P (2010) Super-Resolution Imaging (CRC Press, Boca Raton, FL).

Moon S, Keles HO, Ozcan A, et al. Integrating microfluidics and lensless imaging for point-of-care testing. Biosensors and Bioelectronics. 2009;24(11):3208-3214. doi: 10.1016/j.bios.2009.03.037.

Moscelli N, van den Driesche S, Witarski W, Pastorekova S, Vellekoop MJ. An imaging system for real-time monitoring of adherently grown cells. Sensors and Actuators A: Physical. 2011;172(1):175-180. doi: 10.1016/j.sna.2011.05.010.

Mudanyali O, Tseng D, Oh C, et al. Compact, light-weight and cost-effective microscope based on lensless incoherent holography for telemedicine applications. Lab Chip. 2010;10(11):1417-1428. http://dx.doi.org/10.1039/C000453G. doi: 10.1039/C000453G.

Ng DC, Tokuda T, Nakagawa T, et al. A new neural imaging approach using a CMOS imaging device. Conf Proc IEEE Eng Med Biol Soc. 2006;1:1061-1064. doi: 10.1109/IEMBS.2006.260316.

Ng DC, Tamura H, Mizuno T, et al. An implantable and fully integrated complementary metal-oxide semiconductor device for in vivo neural imaging and electrical interfacing with the mouse hippocampus. Sensors and Actuators A: Physical. 2008;145-146(0):176-186. doi: 10.1016/j.sna.2007.11.020.

Ng, D, Tokuda T, Shiosaka S, Tano Y, Ohta J. Implantable microimagers. Sensors. 2008;8(5):3183-3204. http://www.mdpi.com/1424-8220/8/5/3183.

Oh C, Isikman SO, Khademhosseinieh B, Ozcan A. On-chip differential interference contrast microscopy using lensless digital holography. Opt Express. 2010;18(5):4717-4726. http://www.opticsexpress.org/abstract.cfm?URI=oe-18-5-4717.

Ohta J, Tagawa A, Minami H, et al. A multimodal sensing device for fluorescence imaging and electrical potential measurement of neural activities in a mouse deep brain. Engineering in Medicine and Biology Society, 2009 EMBC 2009 Annual International Conference of the IEEE. 2009:5887-5890. doi: 10.1109/IEMBS.2009.5334461.

Pang S, Han C, Kato M, Sternberg PW, Yang C. Wide and scalable field-of-view talbot-grid-based fluorescence microscopy. Opt Lett. 2012;37(23):5018-5020. doi: 10.1364/OL.37.005018.

Prakash SB, Nelson NM, Haas AM, et al. BioLabs-on-A-chip: Monitoring cells using CMOS biosensors. Life Science Systems and Applications Workshop, 2006 IEEE/NLM. 2006:1-2. doi: 10.1109/LSSA.2006.250426.

(56) References Cited

OTHER PUBLICATIONS

Psaltis D, Quake SR, Yang C. Developing optofluidic technology through the fusion of microfluidics and optics. Nature. 2006;442(7101):381-386. http://dx.doi.org/10.1038/nature05060.

Reale L, Bonfigli F, Lai A, et al. X-ray microscopy of plant cells by using LiF crystal as a detector. Microsc Res Tech. 2008;71(12):839-848. http://europepmc.org/abstract/MED/18785247.

Richard C, Renaudin A, Aimez V, Charette PG. An integrated hybrid interference and absorption filter for fluorescence detection in lab-on-a-chip devices. Lab Chip. 2009;9(10):1371-1376. doi: 10.1039/b819080a; 10.1039/b819080a.

Rodenburg JM, Hurst AC, Cullis AG. Transmission microscopy without lenses for objects of unlimited size. Ultramicroscopy. 2007;107(2-3):227-231. doi: 10.1016/j.ultramic.2006.07.007.

Salama K, Eltoukhy H, Hassibi A, El-Gamal A. Modeling and simulation of luminescence detection platforms. Biosens Bioelectron. 2004;19(11):1377-1386. doi: 10.1016/j.bios.2003.12.031.

Sander D, Dandin M, Honghao Ji, Nelson N, Abshire P. Low-noise CMOS fluorescence sensor. Circuits and Systems, 2007 ISCAS 2007 IEEE International Symposium on. 2007:2007-2010. doi: 10.1109/ISCAS.2007.378431.

Seo S, Su T, Tseng DK, Erlinger A, Ozcan A. Lensfree holographic imaging for on-chip cytometry and diagnostics. Lab Chip. 2009;9(6):777-787. http://dx.doi.org/10.1039/B813943A. doi: 10.1039/B813943A.

Singh RR, Ho D, Nilchi A, Genov R, Gulak PG. A hybrid thin-film/CMOS fluorescence contact imager. Circuits and Systems, 2009 ISCAS 2009 IEEE International Symposium on 2009:24372440. doi: 10.1109/ISCAS.2009.5118293.

Singh RR, Ho D, Nilchi A, Gulak PG, Yau P, Genov R. A CMOS/Thin-film fluorescence contact imaging microsystem for DNA analysis. Circuits and Systems I: Regular Papers, IEEE Transactions on. 2010;57(5):1029-1038. doi: 10.1109/TCSI.2010.2043990.

Singh RR, Leng L, Guenther A, Genov R. A hybrid CMOS-microfluidic contact imaging microsystem. . 2009:739712-739712. doi: 10.1117/12.827862.

Su TW, Seo S, Edinger A, Ozcan A. High-throughput lensfree imaging and characterization of a heterogeneous cell solution on a chip. Biotechnol Bioeng. 2009;102(3):856-868. doi: 10.1002/bit.22116; 10.1002/bit.22116.

Tam T, Jullien GA, Yadid-Pecht O. A CMOS contact imager for cell detection in bio-sensing applications. Circuits and Systems, 2007 ISCAS 2007 IEEE International Symposium on. 2007:813-816. doi: 10.1109/ISCAS.2007.378030.

Tokuda T, Ng DC, Yamamoto A, Kagawa K, Nunoshita M, Ohta J. A CMOS optical/potential image sensor with 7.5μm pixel size for on-chip neural and DNA spot sensing. Engineering in Medicine and Biology Society, 2005 IEEE-EMBS 2005 27th Annual International Conference of the. 2005:7269-7272. doi: 10.1109/IEMBS.2005.1616189.

Tseng D, Mudanyali O, Oztoprak C, et al. Lensfree microscopy on a cellphone. Lab Chip. 2010; 10(14):1787-1792. http://dx.doi.org/10.1039/C003477K. doi: 10.1039/C003477K.

Wang A, Gill P. Molnar A. Light field image sensors based on the talbot effect. Appl Opt. 2009;48(31):5897-5905. http://ao.osa.org/abstract.cfm?URI=ao-48-31-5897.

Zheng G, Lee SA, Yang S, Yang C. Sub-pixel resolving optofluidic microscope for on-chip cell imaging. Lab Chip. 2010;10(22):3125-3129. http://dx.doi.org/10.1039/C0LC00213E. doi: 10.1039/C0LC00213E.

Zheng G, Cui X, Yang C. Surface-wave-enabled Darkfield aperture for background suppression during weak signal detection. Proceedings of the National Academy of Sciences. 2010. doi: 10.1073/pnas.0912563107.

Zheng G, Lee SA, Antebi Y, Elowitz MB, Yang C. The ePetri dish, an on-chip cell imaging platform based on subpixel perspective sweeping microscopy (SPSM). Proceedings of the National Academy of Sciences. 2011. doi: 10.1073/pnas.1110681108.

Voluntary amendment filed with English translation of Chinese Application No. 201080059753.X filed Feb. 7, 2013 (17 pages).

Office action with English translation from Chinese Application No. 201080059753.X dated Dec. 25, 2013 (19 pages).

Response to European Communication dated Jun. 6, 2012 in European application No. 10827423.4, filed Dec. 10, 2012 (15 pages).

Lee, Seung Ah, et al., "Supplementary Information for: Sub-pixel resolving optofluidic microscope for on-hip cell imaging", Supplementary Material (ESI) for Lab on a Chip, the Royal Society of Chemistry, 2012 (4 pages).

Cetin, Arif E., et al., "Handheld high-throughput plasmonic biosensor using computational on-chip imaging", Light: Science & Applications, e122, doi:10.1038/lsa.2014.3, 2014 (10 pages).

Office action with English translation dated Apr. 2, 2014 in Japanese application 2012-536989 (12 pages).

Entcheva, Emilia, et al., "Contact Fluorescence Imaging of Reentry in Monolayers of Cultured Neonatal Rat Ventricular Myocytes", Department of Biomedical Engineering, The Johns Hopkins University School of Medicine, Baltimore, Maryland, Journal of Cardiovascular Electrophysiology, vol. 11, No. 6, pp. 665-676, Jun. 2000 (13 pages).

Entcheva, Emilia, et al. "Fluorescence Imaging of Electrical Activity in Cardia Cells Using an All-Solid-State System", IEEE Transactions on Biomedical Engineering, vol. 51, No. 2, pp. 333-341, Feb. 2004 (9 pages).

Entcheva, Emilia, et al, "Macroscopic optical mapping of excitation in cardiac cell networks with ultra-high spatiotemporal resolution", Progress in Biophysics & Molecular Biology, vol. 92, pp. 232-257, 2006 (26 pages).

Liu, Yingkai, et al., "Cell-lab on a chip: a CMOS-Based Microsystem for Culturing and Monitoring Cells", Proceedings of the 26thAnnual International Conference of the IEEE EMBS, San Francisco, CA, pp. 2534-2537, Sep. 1-5, 2004 (4 pages).

Lu, Steven N., et al., "Optical Mapping of Anatomical Reentry in Monolayers of Cultured Neonatal Rat Cardiac Myocytes", Proceedings of the First Joint BMES/EMBS Conference, Serving Humanity, Advancing Technology, Oct. 1346, 1999 (1 page).

Ng, David, et al., "Integrated in Vivo Neural Imaging and Interface CMOS Devices: Design, Packaging, and Implementation", IEEE Sensors Journal, vol. 8, No. 1, pp. 121-130, Jan. 2008 (10 pages).

Barda Broad Agency Announcement for the Addvanced Research and Development of Chemical, Biological, Radiological, and Nuclear Medical Countermeasures, "Development of a Rapid, Point-of-Care Biodosimeter to Determine Absorbed Radiation Dose", White Paper for Research Areas 6.1 and 6.2 (Biodosimetry Diagnostics), Jun. 7, 2013 (13 pages).

Zheng, Guoan, et al., "Scanning Projective Microscopy for 2D and 3D imaging", Electrical Engineering, California Institute of Technology, 2011 (5 pages).

Rojas-Palma, Carlos, "Triage, Monitoring and Treatment Handbook," 2009 (290 pages).

Certified PCT application No. PCT/JP2007/000401 filed Apr. 26, 2006 (22 pages).

Optofluidics, "Optofluidic microscope shrinks to fit on a chip", optics.org/ole, Oct. 2008 (2 pages).

Sadrozinski, Harmut F, et al., "The Particl Tracking Silicon Microscope PTSM", Nov. 15, 2003 (5 pages).

Cabello, Jorge, et al., "Digital autoradiography using room temperature CCD and CMOS imaging technology", Phys. Med. Biol. 52 (2007), 4993-5011 (19 pages).

Waselenko, Jamie K., "Medical Management of the Acute Radiation Syndrome: Recommendations of the Strategic National Stockpile Radiation Working Group", Annual Internal Medicine, 2004 (19 pages).

American Red Cross, "Planning Guidance for Response to a Nuclear Detonation", Jun. 2010 (135 pages).

Nakayama, Yasuhiro, "Varied Effects of Thoracic Irradiation on Peripheral Lymphocyte Subsets in Lung Cancer Patients", Internal Medicine vol. 34, No. 10, Oct. 1995 (7 pages).

Goans, Ronald E., et al., "Early Dose Assessment in Criticality Accidents", Health Physics Society, 2001 (4 pages).

(56) References Cited

OTHER PUBLICATIONS

Goans, Ronald E., et al., "Early Dose Assessment Following Severe Radiation Accidents", Health Physics, 72(4):513-518, Apr. 1997, abstract (1 page).
Baranov, AE., et al., "Chernobyl experience: biological indictors of exposure to ionizing radiation", Stem Cells, 13 Suppl 1:69-77, May 1995 (2 pages).
Koenig, Kristi L., et al., "Medical Treatment of Radiological Casualties: Current Concepts", Disaster and Terrorism/Review Article, Jan. 20, 2005 (10 pages).
Williams, Jacqueline P., "Animal Models for Medical Countermeasures to Radiation Exposure", National Institute of Health, Apr. 2010 (35 pages).
Ivashkevich, Alesia N. et al., "γH2AX foci as a measure of DNA damage: A computational approach to automatic analysis", Mutation Research 711, 49-60, 2011 (12 pages).
Farsiu, Sina, et al., "Multiframe Demosaicing and Super-Resolution of Color Images", IEEE Transactions on Image Processing, vol. 15, No. 1, Jan. 2006 (19 pages).
Vaurijoux, Aurelie, et al., "Biological Dosimetry of Ionizing Radiation", Laboratory of Biological Dosimetry, www.intechopen.com, Feb. 12, 2012 (21 pages).
Swartz, Harold, M., et al., "A Critical Assessment of Biodosimetry Methods for Large-Scale Incidents", vol. 98, No. 2, Feb. 2010 (14 pages).
Alexander, George A., et al., "BiodosEPR-2006 Meeting: Acute dosimetry consensus committee recommendations on biodosimetry applications in events involving uses of radiation by terrorists and radiation accidents", Science Direct, 2007 (25 pages).
Seo, Sungkyu, et al., "High-Throughput Lens-Free Blood Analysis on a Chip", Anal. Chem. 82, 4621-4627, 2010 (7 pages).
Mudanyali, Onur, et al., "Lenless On-Chip Imaging of Cells provides a new tool for high-throughout cell-biology and medical diagnostics", Journal of Visualized Experiments, 2009 (3 pages).
Webster, J.R., et al., "Monolithic Electrophoresis Device with Integrated Fluorescence Detector", Anal. Chem. 1622-1626, 2001 (5 pages).
Mudayali, Onur, et al., "Compact, light-weight and cost-effective microscope based on lensless incoherent holography for telemedicine applications", Lab on a Chip, 2010 (20 pages).
International Search Report and Written Opinion mailed Jul. 17, 2014 from corresponding PCT Application No. PCT/CA2014/050070 (4 pages).
Baranov, A.E. et al., "Use of Blood Cell Count Changes after Radiation Exposure in Dose Assessment and Evaluation of Bone Marrow Function", Institute of Biophysics, Ministry of the USSR, Moscow, USSR, 1990 (17 pages).
Response to Office action with English translation from Chinese Application No. 201080059753.X filed Jul. 9, 2014 (12 pages).
Response with English translation to Japanese Office action filed in Japanese application 2012-536989 filed on Sep. 30, 2014 (29 pages).
Chinese office action with English translation from Chinese Application 201080059753.X dated Nov. 17, 2014 (4 pages).
Response to Office action with English translation from Chinese application No. 201080059753.X filed on Feb. 2, 2015 (13 pages).
Decision of Rejection with English translation from Japanese application 2012-536989 issued on Mar. 2, 2015 (11 pages).
Chinese Office Action with English translation from Chinese application 201080059753.X issued on May 7, 2015 (5 pages).
Japanese Notice of Reasons for Rejection, with translation thereof, for JP Appl No. 2015-132271, dated Aug. 1, 2016. (12 pages).
Chinese Office Action with English translation from Chinese application 201080059753.X dated Sep. 15, 2015. (6 pages).
Canadian Office Action from Canadian application 2778725 dated Nov. 22, 2016 (4 pages).
European Communication from European application 14749668.1 issued on Nov. 7, 2016 (5 pages).
Chinese Office Action with English translation from Chinese application 201610217300.4 dated Aug. 30, 2017 (7 pages).
Response to Chinese Office Action in Chinese application 201610217300.4 dated Aug. 30, 2017, filed on Jan. 9, 2018 (12 pages).

European Supplemental Search Report issued in European application 10827423.4 on Jul. 12, 2017 (19 pages).
Good, B.T., et al., "An effervescent reaction micropump for portable microfluidic systems", Lab on a Chip, Royal Society of Chemistry, vol. 6, No. 5, Jan. 1, 2006 (Jan. 1, 2006), pp. 659-666, XP002577744, ISSN: 1473-0197, DOI: 10.1O39/B601542E [retrieved on Mar. 20, 2006].
Ozcan, Aydogan: Lensfree on-chip imaging for telemedicine applications, Optical MEMS and Nanophotonics, 2009 IEEE/LEOS International Conference on, IEEE, Piscataway, NJ, USA, Aug. 17, 2009 (Aug. 17, 2009), pp. 59-60, XP031570125, ISBN: 978-1-4244-2382].
Ozcan, Aydogan et al.,: "Ultra-wide-field lens-free monitoring of cells on-chip", Lab on a Chip, vol. 8, No. 1, Jan. 1, 2008 (Jan. 1, 2008), p. 98, XP055051174, ISSN: 1473-0197, DOI: 10.1039/B713695A.
Ting-Wei Su et al: "24: OPN 2008 Towards Wireless Health: On-Chip Cytometry", Dec. Lensless 16,21-25, Dec. 30, 2008 (Dec. 30, 2008), XP055419182, Retrieved from the Internet: URL:https://www.osapublishing.org/DirectPDFAccess/472D83FE-B727-F2F7-7A63B2F4FBF0B3AD_175086/opn-19-12-24.pdf?da=1&id=175086&seq=0&mobile=no [retrieved on Oct. 25, 2017].
European Communication issued in European application No. 10827423.4 on Dec. 11, 2017 (13 pages).
Response to Japanese Notice of Reasons for Rejection, with English translation thereof, for JP Appl No. 2015-132271, filed on Jan. 31, 2017 (29 pages).
Japanese Notice of Reasons for Rejection, with translation thereof, for JP Appl No. 2015-132271, dated Jun. 14, 2017. (17 pages).
Canadian Office Action issued in Canadian application 2938896 dated Jul. 11, 2017 (31 pages).
Response to Canadian Office Action submitted in Canadian application 2938896 dated Jan. 11, 2018 (125 pages).
European Search Report issued in European application 14749668.1 dated Oct. 24, 2016 (6 pages).
Response to European Communication from European application 14749668.1 submitted on Feb. 21, 2017 (29 pages).
Japanese Office Action with English translation issued in Japanese application 2015-556353 dated Nov. 27, 2017 (14 pages).
International Preliminary Report on Patentability mailed Aug. 20, 2015 from corresponding PCT Application No. PCT/CA2014/050070 (11 pages).
Isikman et al., "Lensfree computational microscopy tools for cell and tissue imaging at the point-of-care and in low-resource settings". Analytical Cellular Pathology, vol. 35 pp. 229-247, 2012.
Kim et al., "LED and CMOS image sensor based hemoglobin concentration measurement technique". Sensors and Actuators B, vol. 157, pp. 103-109, 2011.
Stybayeva et al., "Lensfree holographic imaging of antibody microarrays for high-throughput detection of leukocyte Nos. And function". Analytical Chemistry, vol. 82(9): 3736-3744, 2010.
Lee et al., "Color capable sub-pixel resolving optofluidic microscope and its application to blood cell imaging for malaria diagnosis". PLOS ONE, vol. 6(10):e23427, 2011.
Mudanyali et al., "Compact and cost-effective lensless telemedicine microscopy for global health applications". IEEE Global Humanitarian Technology Conference, pp. 62+-65, 2011.
International Search Report and Written Opinion for corresponding PCT/CA2014/050610, dated Sep. 16, 2014.
International Preliminary Report on Patentability for corresponding PCT/CA2014/050610, dated Dec. 29, 2015.
Voluntary amendment with English translation filed in CN Application 201480047483.9 on Jun. 27, 2016 (21 pages).
European Communication Pursuant to Rules 161(2) & 162 EPC issued in European application 14817587.0 on Feb. 9, 2016 (2 pages).
Response to European Communication Pursuant to Rules 161(2) & 162 EPC issued in European application 14817587.0 submitted on Jun. 28, 2016 (5 pages).
Supplemental Search Report from European application 14817587.0 issued on Jan. 26, 2017 (9 pages).
European Communication Pursuant to Rules 70(2) and 70a(2) EPC issued in European application 14817587.0 on Feb. 14, 2017 (1 page).
Response to European Communication Pursuant to Rules 70(2) and 70a(2) EPC issued in European application 14817587.0 submitted on Aug. 18, 2017 (14 pages).

(56) References Cited

OTHER PUBLICATIONS

European Communication pursuant to Article 94(3) EPC issued in European Application 14817587.0 on Oct. 26, 2017 (5 pages).
Japanese Office action issued in Japanese application 2016-522155 dated Feb. 19, 2018 (7 pages).
Response to Japanese Office action with English translation issued in Japanese application 2015-556353 submitted on Feb. 27, 2018 (8 pages).
PAIR transaction history of US Provisional Serial No. 61/255,781 filed on Oct. 28, 2009 as of Feb. 26, 2018.
PAIR transaction history of U.S. Appl. No. 12/913,639, filed on Oct. 27, 2010.
PAIR transaction history of U.S. Appl. No. 14/698,532, filed on Apr. 28, 2015.
PAIR transaction history and application as filed includes pending claims (2017/0322402) of US Appl. No. 15/642,434 filed on Jul. 6, 2017 as of Feb. 26, 2018.
PAIR transaction history and issued claims (included in 9,075,225) of U.S. Appl. No. 13/095,175, filed on Apr. 27, 2011 as of Feb. 26, 2018.
PAIR transaction history, application as filed and pending claims of U.S. Appl. No. 14/710,046, filed on May 12, 2015.
PAIR transaction history and application as filed for US provisional 61/761,467 filed on Feb. 6, 2013.
PAIR transaction history and application as filed for US provisional 61/785,762 filed on Mar. 14, 2013.
PAIR transaction history, application as filed and pending claims of U.S. Appl. No. 14/173,500, filed on Feb. 5, 2014 as of Feb. 26, 2018.
PAIR transaction history and application as filed of US Provisional Application 61/839,735 filed on Jun. 26, 2013.
PAIR transaction history, application as filed and issued claims (included in 9,518,920) of U.S. Appl. No. 14/314,743, filed on Jun. 25, 2014 as of Mar. 5, 2018.
PAIR transaction history and application as filed for US provisional application 62/131,164 filed on Mar. 10, 2015 as of Feb. 26, 2018.
PAIR transaction history and application as filed with pending claims (included in 2016/0187235) for U.S. Appl. No. 15/066,065 filed on Mar. 10, 2016 as of Feb. 26, 2018.

* cited by examiner

SAMPLE PROCESSING IMPROVEMENTS FOR MICROSCOPY

This application is a divisional application and claims priority under 35 U.S.C. § 120 to U.S. patent application Ser. No. 14/314,743, filed Jun. 25, 2014, which claims the benefit of U.S. Provisional Patent Application No. 61/839,735, filed Jun. 26, 2013, which is related to U.S. patent application Ser. 61/255,781, filed Oct. 28, 2009; Ser. No. 12/913,639, filed Oct. 27, 2010; Ser. No. 13/095,175, filed Apr. 27, 2011; 61/761,467, filed Feb. 6, 2013; and 61/785,762, filed Mar. 14, 2013. Those applications are incorporated by reference here in their entireties.

This disclosure relates to sample processing improvements for microscopy.

In a typical optical microscope, light that passes through a sample is delivered to the eye of a user, or film, or a sensor through lenses that form an image that is representative of the sample.

In other approaches, light representative of a sample can be detected and used to form an image of the sample without lenses by placing the sample on or near a detector, for example, an integrated circuit, that includes an arrangement of light sensitive elements. Signals generated by the detector can be processed to derive an image.

SUMMARY

In general, in an aspect, one surface of a microscopy sample chamber is moved to a distance from another surface of the sample chamber that will enable capillary flow of a fluid containing a sample within the chamber. After the capillary flow, the one surface is moved closer to the other surface to a distance that forces the sample against the other surface for high resolution digital microscopy.

Implementations may include one or any combination of two or more of the following features. The moving of the surface toward the other surface is controlled automatically. The fluid is ejected into the sample chamber before moving the one surface closer to the other surface. The fluid is ejected automatically. The moving of the surface toward the other surface is controlled automatically.

In general, in an aspect, there is a chamber to contain a fluid sample for use in microscopy, and a mechanism to controllably deliver the sample to a location of the chamber to enable the sample to be drawn across the chamber by capillary action.

Implementations may include one or any combination of two or more of the following features. There is a hydrophilic coating on a wall of the chamber. There is a sensor exposed in the chamber and the apparatus includes a hydrophilic hydrophobic coating of areas in the vicinity of the sensor. The mechanism includes a feature of the chamber to cooperate with a feature of pipette. The feature of the pipette includes a tip and the feature of the chamber includes a guide for the tip, at an edge of the chamber. The feature of the pipette includes a tip and the feature of the chamber includes a hole to receive the tip and to deliver the sample from the tip to a predefined location in the chamber. The feature of the pipette and the feature of the chamber are configured to mate. The mechanism includes an automatically controlled pumping or mixing device.

In general, in an aspect, a characteristic of light absorber within an element of a sample is determined from signals produced by pixels of a high resolution sensor when the sample is illuminated by light of a wavelength that corresponds to optical characteristics of the absorber. The determining includes determining an aggregate absorption of the light by the absorber within the element by averaging intensities for the pixels associated with the element of the sample. Background light intensity is determined based on intensities for pixels near the element of the sample. A model of the element is used to estimate a path length of the light passing through the element. The characteristic of the absorber is determined using Beer's law.

Implementations may include one or any combination of two or more of the following features. Deviations from Beer's law caused by uneven thickness, lensing, or scattering are corrected. A forward scattered signal is used in determining the characteristic of the absorber. The light has a wavelength corresponding to the maximum absorbing wavelength of the element.

In general, in an aspect, a first surface is configured to receive a sample and is to be used in a microscopy device. There is a second surface to be moved into a predefined position relative to the first surface to form a sample space that is between the first surface and the second surface and contains at least part of the sample. There is a mechanism configured to move the second surface from an initial position into the predefined position to form the sample space. When the sample is in place on the first surface, the motion of the second surface includes a trajectory that is not solely a linear motion of the second surface towards the first surface.

Implementations may include one or any combination of two or more of the following features. The trajectory is traversed at a controlled velocity. The trajectory includes an arc. The sample includes elements that are to be counted, and the mechanism is configured so that the trajectory causes the elements to be evenly distributed across a field of view of the microscopy device and causes the bulk concentration of the elements in the sample after the second surface reaches the predefined position to be consistently proportional to the bulk concentration of the elements in the sample when the second surface is in the initial position. The bulk concentration of the elements in the sample after the second surface reaches the predefined position is the same as or higher than the bulk concentration of the elements in the sample when the second surface is in the initial position. The trajectory includes movement of the second surface toward and away from first surface repeatedly before reaching the predefined position to cause mixing of the sample. The second surface has an alignment edge that bears against an alignment edge associated with the first surface to define a pivot axis about which the second surface is to be rotated to reach the predefined position. The alignment edge includes only two points of contact that bear against the alignment edge associated with the first surface. The alignment elements of the first surface and second surface reduce linear motion of the second surface relative to the first surface in each of two orthogonal directions. The mechanism includes a passive mechanism.

In general, in an aspect, a sample volume is formed between two surfaces for use in microscopy by applying a controlled repeatable trajectory of motion between the two surfaces, the trajectory not being solely a linear motion.

Implementations may include one or any combination of two or more of the following features. The trajectory includes an arc. The controlled repeatable trajectory of motion includes a controlled velocity of motion.

In general, in an aspect, an apparatus includes an agent to reduce motion of elements in a sample before or when the sample is subjected to microscopy, and a mechanism for imparting the agent to the sample.

Implementations may include one or any combination of two or more of the following features. The apparatus includes the sample. The agent includes a viscosity increasing agent. The viscosity increasing agent includes at least one of dextran, cellulose derivatives, and glycerol. The agent includes a density increasing agent. The agent increases stickiness of the elements in the sample to a surface used in the microscopy. The agent includes thixotropic agents. The agent includes an agent that is photo cross-linkable or gel-able or both.

In general, in an aspect, a swab is to be dragged along one dimension of a surface of a microscopy device to prepare the surface to receive a sample. The swab has a length that corresponds to a second dimension of the surface that is orthogonal to the one dimension.

Implementations may include one or any combination of two or more of the following features. The swab is configured to clean the surface. The swab includes two or more different features each of which extends the length of the swab. The features include compartments that hold different fluids to contact the surface sequentially as the swab is dragged. The one of the features includes a cleaning agent. The one of the features includes a drying material. A supply of fluid is to be delivered to the swab before use. The supply is held in a container that reduces evaporation or decay of the fluid until it is delivered to the swab.

In general, in an aspect, a concentration of larger diameter elements is increased relative to smaller diameter elements in a sample that contains the larger elements and the smaller elements and is to be held between two surfaces that are to be brought together to contain the sample and are to be used in a microscopy device. The increasing of the concentration includes providing a spacing mechanism that imposes a minimum distance between the two surfaces as they are brought together that is smaller than original diameters of the large elements and larger than original diameters of the smaller elements in the sample. The larger elements comprise white blood cells and the smaller elements comprise red blood cells.

Implementations may include one or any combination of two or more of the following features. The original diameters of larger elements are determined based on their measured areas and the minimum distance between the two surfaces. The counts of larger elements of given original diameters are used to determine a concentration of larger elements of respective original diameters in the sample. An average original concentration of the larger elements is derived from the concentrations of larger elements of respective original diameters.

In general, in an aspect, there are two surfaces at least one of which is movable relative to the other to define a space in which to contain a diluted blood sample. There is a spacing mechanism to cause the space to have a predetermined minimum height when the one surface is moved toward the other. The height is short enough to cause white blood cells to be squeezed between the two surfaces and tall enough to allow red blood cells to move within the diluted sample.

Other features, objects, and advantages of the invention will be apparent from the description and drawings, and from the claims.

DETAILED DESCRIPTION

The figures and elements shown in them are not always to scale and many of them are illustrated schematically. The spatial relationships of the elements in the figure may appear differently than the descriptions in the text, for example, above and below and top and bottom may be shown oppositely in the figures from the way they are described in the text.

Figure 1:
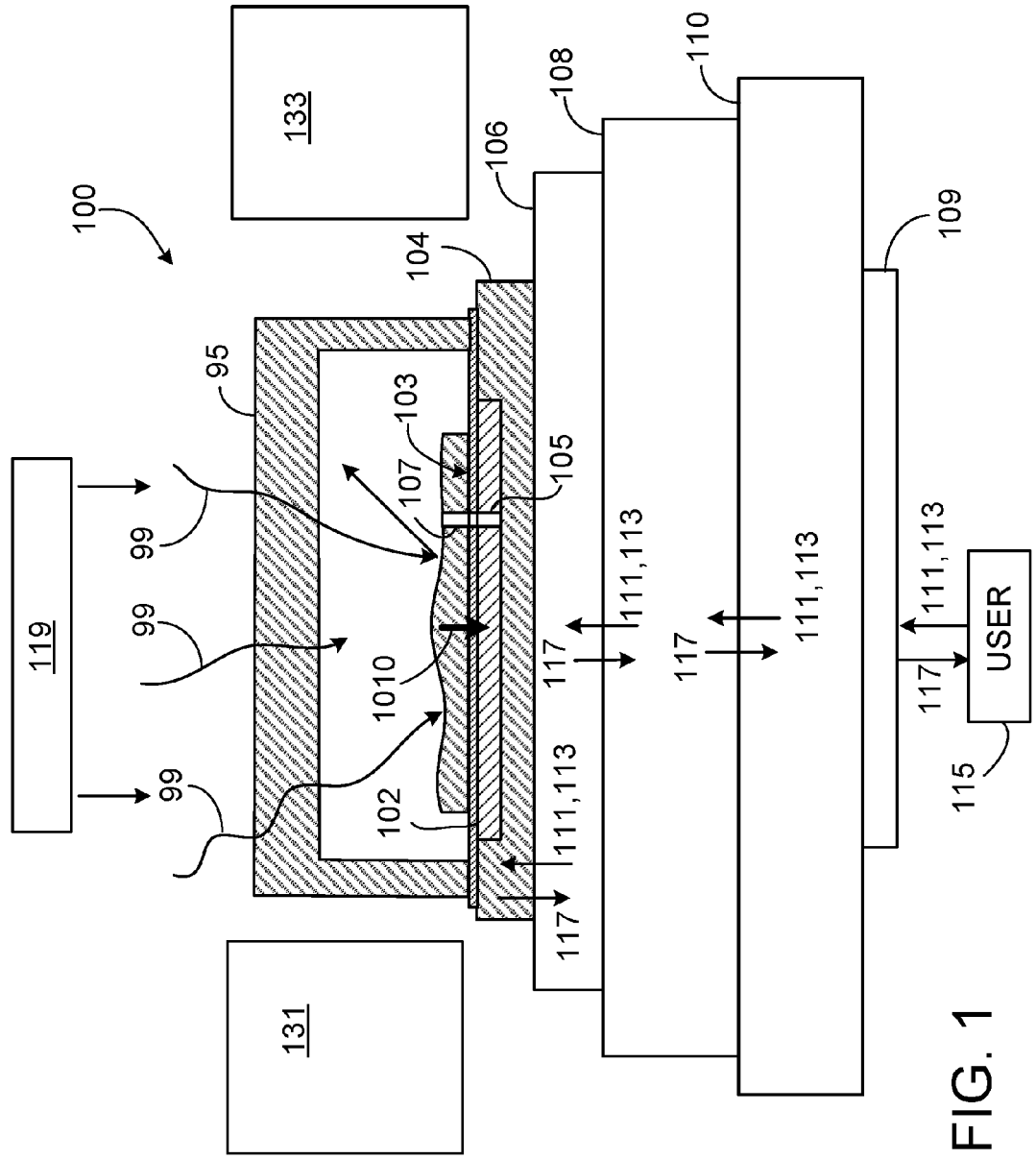
FIG. 1 is a schematic side view partly in section of a system to detect and use light representative of a sample.

As shown in FIG. 1, in some implementations of the concepts that we describe here, a system 100 can capture high resolution images (e.g., full-color, gray-scale, "black-and-white" or a combination of them) of a sample 101 (e.g., a sample in a gas phase, a liquid phase, or a solid phase, or a combination of those or other forms) that is in contact with (or in close proximity to) a light sensor 102. The light sensor includes a two-dimensional arrangement of light sensitive elements 105 that can correspond to an array of pixels in the image. We sometimes refer to the elements of the light sensor as pixels for simplicity.

We sometimes use the phrase "light sensitive locations" in the broadest sense to include, for example any features of a device that are separately sensitive to light or separately capable of emitting light, or both, including light sensitive elements or pixels and light source locations. We sometimes use the phrase light source locations to refer to elements capable of emitting light. In some cases we use the phrase light sensitive location to refer to an exposed light sensitive portion of a feature of the device without any covering, protective layer, shield, or any other feature that might separate the light sensitive from the ambient or from a sample.

We sometimes use the phrase "contact microscope" or "contact microscopy" to refer in the broadest sense to any device (or technique) that includes (a) a high resolution sensor of closely spaced light sensitive or a high resolution set of light emitting locations that are exposed to the ambient at a surface of the device together with (b) a device to associate with that surface a portion of a sample that is to be imaged, and, in the case of light emitting locations, a light detector relatively far from the light emitting locations and sample, so that the portion of the sample is in contact with (or nearly in contact with) the surface and a usable high resolution image can be obtained by the sensor when the portion of the sample is in place.

In contact microscopy, the sample is either in direct contact with the light sensitive features of sensor, or light emitting features of the light source, without any intervening material, or the sample may be nearly in contact with the light sensitive or emitting features. By nearly in contact, we mean, for example, within the near field of the features, in some cases at a distance that is within ½ of the wavelength of the light involved or possibly at a distance that is within a wavelength of the light involved.

We use the concept of a device to associate the sample with the surface in its broadest sense to include any mechanism of any kind that facilitates the movement, flow, delivery, placement, or presentation, for example, of a portion of the sample into contact with or nearly into contact with the light sensitive locations, including any mechanism that uses mechanical, electrical, electromechanical, pneumatic, hydraulic, gravitational, or other features, for example.

Sometimes the amount of sample loaded onto the sensor is larger than the amounted needed for imaging. In some implementations, the sample needs to be in the form of a relatively thin layer, e.g., 1 µm to 100 µm, or have a thickness such that a single layer of cells of the sample is displaced on the sensor for imaging. A lid or cover or chamber or chamber top 95 can be moved (or can descend) to contact the sample and adjust the amount of sample, e.g., the thickness of the sample, on the sensor. As an example, the adjustment can be done by pressing one end of the chamber top 95 against the sample 101 so that the excessive amount of sample flows out of the perimeters of the sensor 102. The chamber top can also descend in other manners. We sometimes refer to the space that is between the surface of the chamber top 95 that has completed its descent and the sensor surface 102 and in which the sample is located a chamber.

The sensor can also include other components either as part of or in addition to the light sensitive elements, to drive or read the elements, generate, process, or deliver signals to and from the elements, and perform other functions. Generally, when we refer to the sensor we mean the integrated circuit or part of it that (a) receives light at light sensitive elements and generates signals or data representing the intensities of light detected by the light sensitive elements, and (b) any electronic elements that directly drive the light sensitive elements or cause the light-generated signals or data to be delivered by the light sensitive elements, but not (c) any other circuitry used to process the signals or data to form the image.

The sensor 102 can be part of or formed on an integrated circuit chip 104, which can be made in a homogeneous fabrication mode or a hybrid fabrication mode. The chip 104 can be mounted on a headboard 106, and the headboard 106 can be part of or be connected to a control unit 108. In some applications, a lid or cover or chamber or chamber wall 95 can abut, touch, surround, enclose, or contain the sample or a portion of it within a space or chamber adjacent to an exposed surface 103 of the sensor or a portion of the headboard or both.

The control unit 108 can be part of or connected to a user device 110. The user device 110 can provide an interface 109 with a user 115; can receive commands 111 and information 113 through the user interface from the user, process them, and forward them to the control unit 108; and can receive information 117 from the control unit, process it, and provide it to the user through the user interface. In some instances, the user interface can operate through the control unit 108 or the headboard 106 or a combination of them and of the user device. And commands and information 111, 113, and 117 can be passed between any two or more of the components.

The system can also include sample transport and management devices 131, 133, that can include mechanical, electrical, or electronic components or combinations of them that enable or cause the sample to be delivered to the sensor, held at the sensor, and removed from the sensor, as needed. The devices 131, 133, can also process the sample before and after imaging including by mixing materials with the sample, removing materials from the sample, fetching the sample from a source, disposing of the imaged sample, and any other function that may be needed with respect to the sample in order to operate the system to perform the imaging.

The user device 110 can be a cell phone, another kind of handheld device, an instrument, a system, a manufacturing component, a work station, or any other user device including one that is dedicated to the function of interacting with the control unit or one that has functions not limited to interaction with the control unit, or a combination of the two.

A complete working system or commercial product or component need not include all of the sensor, the chip, the headboard, the control unit, and the user device, but could include a combination of any two or more of them.

In various implementations, any combination of two or more of the sensor 102, the chip 104, the headboard 106, the control unit 108, and the user device 110 can have a variety of mechanical and electrical connections among them. In addition, mechanical, fluid flow, electronic, software, data processing, communication, storage, and electrical functions needed for various operations can be distributed in a variety of ways between and among pairs and three or more of those parts of the system. The distribution of functions can be arbitrary or based on commercial and technological considerations in a wide variety of ways.

In some instances, the sensor 102, which we use to refer to the light sensitive area of the chip 104, can operate as a charge-coupled device (CCD) or as a complementary metal-oxide semiconductor (CMOS) sensor technology. Other imaging regimes may be possible. As mentioned earlier, in some examples, the sensor is pixelated, that is operates with respect to rows and columns (or other array arrangements) of light sensitive picture elements (pixels) 105.

During operation, the sensor responds to incident electromagnetic radiation (e.g., light) 99 that passes through 1091, is scattered from, or emanates from the sample 101. Light that passes through or is scattered from or emanates from the sample may be altered in wavelength, for example, as it passes through or is scattered or emanates. The incident electromagnetic radiation 99 and the transmitted, scattered, or emanated radiation is typically in the wavelength range of visible light, near ultraviolet, or near infrared. We use the term light in its broadest sense to include all such ranges, for example.

Because the sample 101 is in contact with or essentially in contact with or in close proximity to the surface 103 of the sensor, there may be no need for any optical elements to be used in the system to refract or collimate or redirect the light.

Light from a portion 107 of the sample that is adjacent to a pixel (or is in a path between the incident light 99 and the pixel) will be received largely (in some cases essentially entirely) by that pixel 105.

In this arrangement, the light sensed by the array of pixels of the sensor is directly representative of a corresponding array of portions of the sample and therefore represents in effect an image of the sample, an image that can be of high resolution.

To the extent that the initial source of the light reaching the sensors is in the environment, that light may be ambient light or can be provided by a dedicated light source 119. In some implementations it may be useful to control the illumination of the sample and in particular the uniformity of the illumination by controlling the light source or screening out ambient light or both.

To capture an image of the sample, the sensor is driven and read during a conceptual image capture cycle. During an image capture cycle, the light received by the sensor at all of its pixels is converted to electrical signals (e.g., analog signals or digital values) that are delivered to electronic components of the chip. The signals may be read in parallel or serially depending on the technology. The electrical signal from each of the pixels typically is represented by a quantized intensity value corresponding to the intensity of light sensed by the pixel, within some range such as a range represented by 14-bit digital values. Color information can be obtained in a variety of ways, for example, using bandpass optical filters over multiple adjacent pixels, or sequential imaging with different color illumination, and possibly in other ways. Whatever method is used, the electrical signals that are received from the various pixels in space and/or time together can represent a full-color high-resolution high-dynamic range image of the sample.

In addition to the electronic features of the system, there are mechanical elements discussed below that among other things handle, contain, and illuminate the sample 101.

Some or all of the electronic and mechanical components that form the system, including the sensor, the chip 104, the headboard 106, the control unit 108, the user device 110, and the user interface 109, and combinations of any two or more of them can be produced as individual commercial products and can be either reusable or disposable.

Controlling Sample Volume for Imaging

1. The Sample

Figure 2:
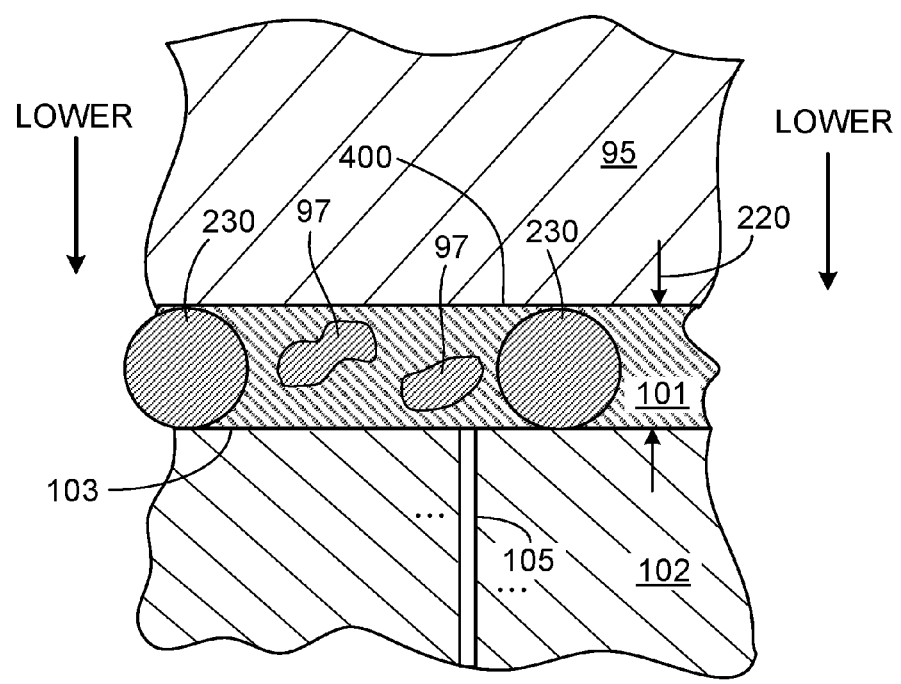
FIGS. 2, 3A, 4A, 4B, 5A, 5B, 7, and 8 are schematic sectional side views of elements useful to detect and use light representative of a sample.

Referring to FIG. 2, the sample 101 (we sometimes use the word specimen interchangeably with the word sample) that is being imaged can be composed of or include small similar types of units 97, such as particles, bits, specks, cells, or molecules, or combinations of them or combinations of any two or more of the different types. The units 97 may be suspended in or carried in a liquid 95 to form liquid-suspended sample units 97, entrained in a gas to form gas-suspended sample units (not shown), rest in an unsuspended and un-entrained form (a powder, for example) on the surface of the sensor (not shown), or be held in an integrated matrix of solid, gelled, or other integral self-supporting material, such as a sectioned layer of tissue, to name only a few examples. We sometimes use the term matrix very broadly to include, for example, any material in which sample units are held, including liquid, gas, solid, gel, or any other material.

Additionally, the sample 101 can also contain spacing feature 230 for controlling the volume of the sample 101 on the sensor 102. In some instances and for a given kind of sample unit or a precisely specified volume of sample (e.g., for a blood count, or other analysis in which the number of sample units is to be counted for a precise volume of the sample), the volume of the sample imaged by the sensor is precisely controlled by the width and length of the top surface of the sensor and by the height of the gap 220 (or the chamber) between that surface and the flat bottom surface of the chamber top. In some cases, the volume may not need to be precise, but the gap height may need to be a precise amount, or no larger than a certain amount, or no smaller than a certain amount, or a combination of those conditions.

A wide variety of techniques and devices can be used to form and maintain a height (e.g., a precise height) of the gap. We broadly refer to those techniques and devices as spacing features. In the example shown in FIG. 2, the spacing feature includes microspheres or other kinds of beads of uniform size, say, 3.0 μm or 5.0 μm. To establish a precise and uniform spacing and therefore volume of the sample space, it may be useful to specify the precision of the bead sizes, for example, the beads could be specified as 4.0 μm with a precision of plus or minus 100 nanometers. The beads can be non-spherical. The beads can be used in a variety of different ways.

As shown in FIG. 2, in some implementations, the beads 230 are included within the sample, for example a sample having a liquid matrix in which sample units (which may be smaller than the beads) are suspended, when the sample is delivered to the sensor surface 103. If the chamber top is then allowed to settle on or be pressed down onto the sample, and assuming that there are enough beads in the sample and they are reasonably well distributed within the liquid, then a uniform accurate gap height can be achieved. For this purpose, the beads might be present in the sample at the rate of 10,000-500,000 beads per microliter of sample, for example. Maintaining an even distribution of the beads in the sample can be done by simple mechanical agitation if the beads are selected to have close to neutral buoyancy in the sample.

In some cases, the beads can be roughly the same size as the sample units. In some implementations, beads of two different sizes can be included. A larger size defines the intended spacing. A smaller size can be counted to verify that the volume of the sample space is as intended, assuming the smaller beads are distributed through the sample reasonably uniformly, and the number of smaller beads per unit volume of the sample is known. The beads may be transparent in order to allow light to pass through to the sensor, or may be colored, or fluorescent, or opaque, or a combination of two or more of those characteristics.

2. The Chamber Top

The chamber top can be lowered relative to the sensor surface 103 to remove the excessive volume of sample from the sensor 102 and allow the sample units 97 (such as cells that are disbursed in a fluid) to be evenly distributed over the surface 103 of the sensor 102. In some implementations, the removal of the excessive volume does not alter the bulk concentration of the sample units so that the imaging of a relatively small volume of the sample, e.g., about 40 μL, produces data applicable to the bulk sample, e.g., about 100 μL or more, dispensed onto the sensor. In other implementations, the new concentration is consistently proportional to the bulk concentration of the sample units, allowing for a correction factor to be determined. To achieve the desired sample concentration for imaging, the sample can be further processed as described further below.

The chamber top can be lowered in various ways. In one example, referring again to FIG. 2, the chamber top has a flat top surface 400 and during the lowering of the chamber top, the top surface 400 is kept substantially parallel to the top surface 103 of the sensor 102. We sometimes call this process a flat, linear descent.

Figure 3A:
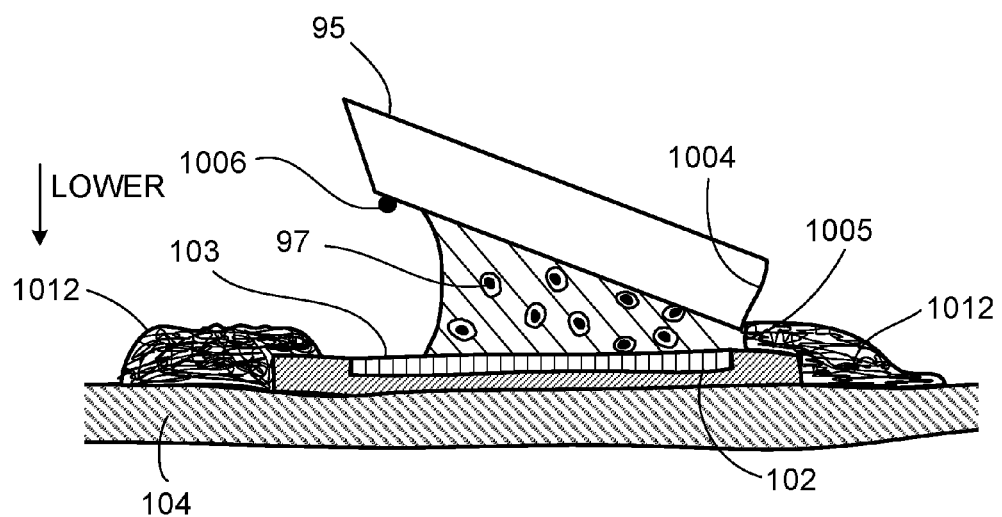
Figure 3B:
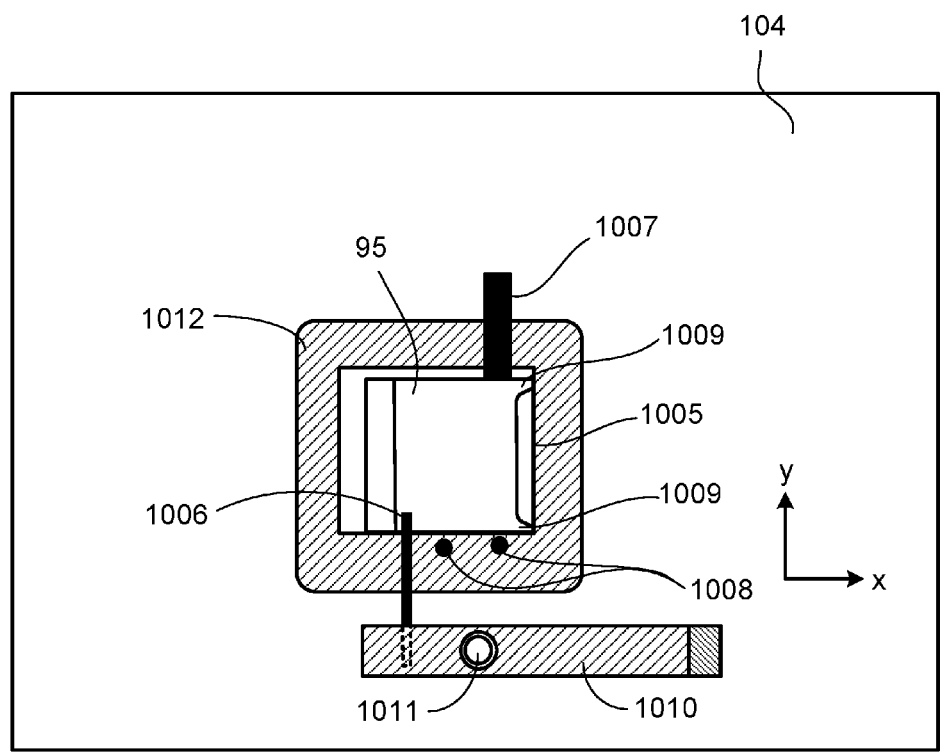
FIGS. 3B, 6A, and 6B are schematic sectional top views of elements useful to detect and use light representative of a sample.

Referring to FIGS. 3 and 4, in another example, the chamber top 95 is positioned initially at a tilt such that one edge is against the sensor. The chamber top is then lowered at a controlled velocity profile until flush with the sensor. We sometimes call this process a pivoting descent. Sometimes data, such as positional variables or parameters, that control the pivoting descent can be chosen and stored, e.g., in a controller. The pivoting descent can be performed repeatability for different imaging processes (of the same sample or different samples) based on the stored data.

The descent of the chamber top can controlled by various mechanisms, e.g., manually by a human or by a machine such as an actuator 1010. In some implementations, after one end of the chamber top is lowered and the chamber top becomes in contact with the sample, the other end of the chamber can be raised and lowered repeatedly, e.g., without coming all the way down to its final position. This operation may cause the sample to rush in and out of the space between the sensor 102 and the chamber top 95, which may provide a mixing effect to the sample so that the sample units 97 are well distributed, e.g., evenly distributed, in the sample before being imaged.

In some implementations, the bottom of the chamber top has a straight edge 1004 that presses against a straight ridge with a vertical wall 1005 on the bottom surface of the chamber. The wall can be formed of encapsulation epoxy deposited on the surface 103 of the image sensor chip 103 and the circuit board 104. The linear points of contact between the edge 1004 and the ridge can serve as a hinge for lowering or raising the chamber top 95.

As an example of use, after the sample is deposited onto the bare sensor, the chamber top is held up at an angle by another point-of-contact 1006 elsewhere and slid forward until the edge 1004 is pushed against the encapsulation ridge of the wall 1005 such that it cannot slide further. The hinge allows the rotational twist of the chamber top in the x-direction consistent from sample to sample or test to test. The chamber top is then slid along the ridge until an adjacent edge of the chamber top hits another barrier 1007 (e.g., either also part of the encapsulation or a separate construction off to the side). This allows the positioning of the chamber top in the y-direction repeatable from test to test (or sample to sample). Then the point of contact 1006 holding up the chamber top is lowered, allowing the chamber top to hinge down until flush with the sensor. In some implementations, the point of contact is lowered in such a way that its friction with the chamber top provides a small force that pushes the chamber top against the ridge, rather than pulling it away, to reduce or avoid disturbance to the position of the chamber top at the wall 1005. It is possible that the chamber top may slide after being placed on (or descended to) the sensor and when the sample is expelled from the chamber. Sometimes guide posts 1008 and/or walls off to the side of the sensor are used to minimize the travelable distance for the chamber top.

In some implementations, the contacting edge 1004 of the chamber top has two extending points at opposite ends 1009 to minimize the amount of the sample that flows into the hinge. The sample flown into the hinge may cause the sample units (such as cells) to be crushed or trapped during the descent of the chamber top.

The actuator 1010 to lower the chamber top can be a passive device that is not fixed to the chamber top. The chamber top may merely rest on the actuator and descend via gravity or another force such as magnetism, electromagnetism, spring, etc. Velocity profile of descent can be controlled by various means, such as including a rotating counterweight, a dash-pot 1011, magnet, electromagnet, etc.

Although the chamber top is described to descend towards a sensor surface, the mechanisms described can be used with any surface, such as a glass slide, in implementations, such as counting cells or other particles using standard microscopy.

Sample Preparation

As explained previously, it may be desirable that the sample unit concentration of the sample being imaged is the same as or has a known relationship to the bulk concentration of the sample units that are dispensed to the sensor surface.

In some situations, the sample units and the beads are heavier than the other fluidic components of the sample, such as a diluent, and are prone to accumulating (as contrast to flowing or moving) when a force is applied to the sample.

The force may be gravity, which may cause sedimentation concentration gradients in the diluted sample, as the sample units sink toward the bottom of the sample. The force can also originate from the descending chamber top. As the chamber top moves, e.g., accelerates, the sample outside the perimeter of the sensor 102, the heavier, suspended sample units have more momentum than the fluid and may not move or accelerate as quickly as the other parts of the sample. The sample units may be left on the sensor in a higher concentration than the bulk concentration in the sample dispensed to the sensor and before the excessive volume of the sample is removed. Furthermore, the force may also include friction force between the sample and the surfaces of the system or shear force within the sample. The friction force and the shear force may reduce the speed of the sample units relative to the sample flow.

Additionally, after the chamber top completes its descent, the sample may continue to flow, causing the sample units to move and disrupting their imaging.

In some implementations, the viscosity of the sample may be adjusted to control the concentration of the sample units and reduce the flow of the sample during imaging. In some examples, the adjustment can be done by adding one or more viscosity-controlling agents to the sample. The sedimentation rates of the sample units can be reduced and the fluid can be allowed to exert a stronger force on the spacer beads and the sample units to counter their momentum and friction. The increased viscosity also can reduce the likelihood of flow after the chamber top completes its descent.

Suitable agents can include dextran, glycerol, starch, cellulose derivatives such as methyl cellulose, any combination of these materials, and other materials.

Alternatively or additionally, one or more agents can be added to the sample to increase diluent density so that the difference in density between the diluent and the spacer beads and/or the sample units is reduced or even eliminated. The reduced or eliminated density difference can also control the concentration of the sample units and reduce the flow of the sample during imaging.

The agent for increasing the diluent density can be the same agent as the viscosity-controlling agent. In some implementations, thixotropic agents can be used to achieve the same effects, and also allow for easier mixing of the sample units with the diluent. In some situations, photo-cross-linkable agent(s) or gelling agent(s) (e.g., temperature dependent, such low-melting-point agarose) can be used to increase the sample viscosity while allowing for easy mixing of the sample units and the diluent.

Cleaning the Contact Microscopy Sensor

Figure 4A:
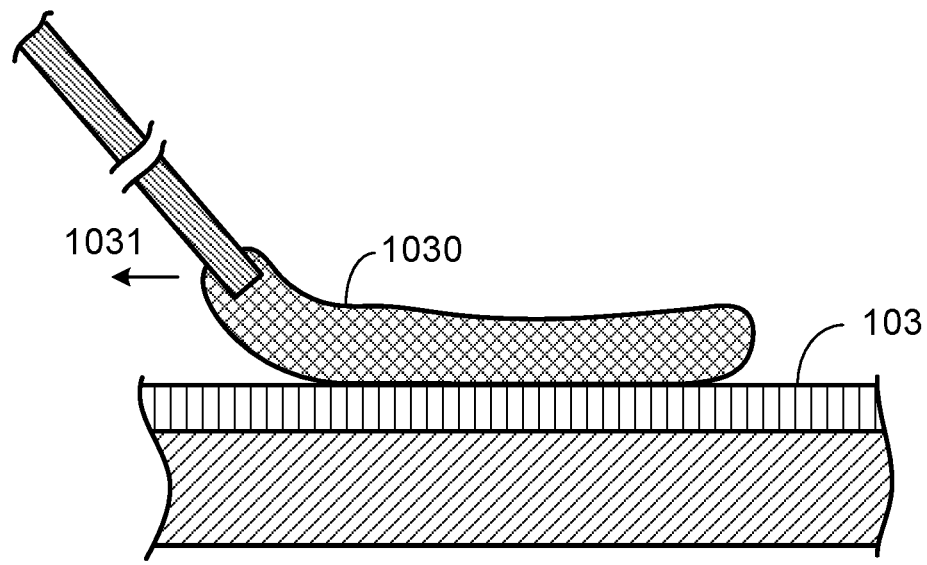
Figure 4B:
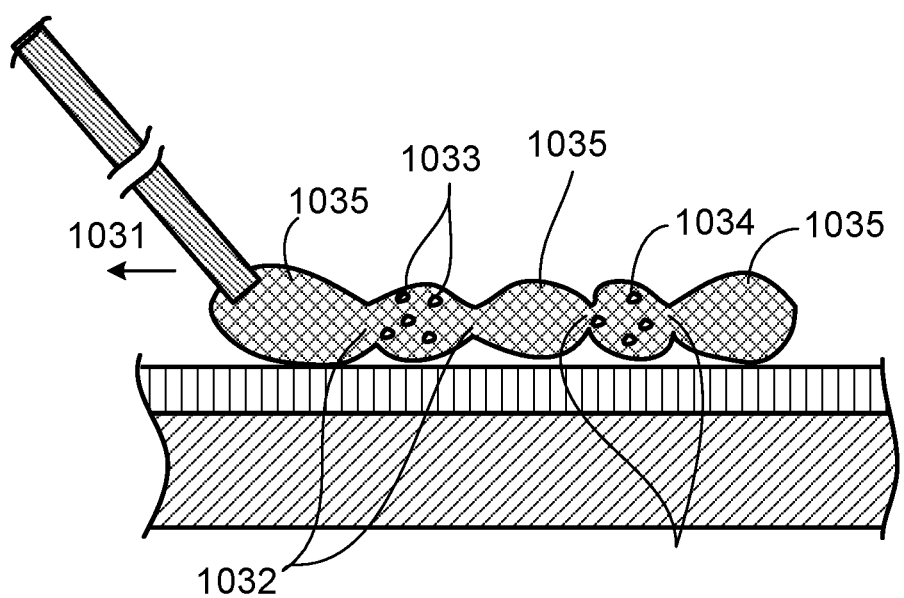

Referring to FIGS. 4A and 4B, before loading a new sample onto the sensor surface 103, the previously imaged sample is removed and the sensor surface 103 is cleaned. The removal and the cleansing can be done in various ways. In one example, a lint-free absorbent swab 1030 having a width similar to the sensor is dragged (1031) along the sensor surface. At one or more moments during the drag, the swab encapsulates the sensor so that the swab and the sensor surface form shallow angles throughout the entire sensor surface. We may also refer to such contacts between the swab and the sensor surface encapsulation contacts. With the encapsulation contacts, the swab has good access to all surfaces of the sensor without scrubbing the surfaces.

In some implementations, some regions of the swab are loaded (or preloaded) with cleaning agent(s) 1034, such as surfactants, organic solvents, or purified water. Other regions 1035 can be left dry and absorbent. The cleaning agent(s) can be stored in separated compartments 1032 of the swab, e.g., in the form of microcapsules 1033 or others. The microcapsules 1033 can be broken by compression immediately before or during the use of the swab, allowing the cleaning agent(s) to wet or saturate the swab. The use of the microcapsules can prevent the cleaning agent(s) from evaporating during storage of the swab. These fluid regions can be arranged in a particular sequence based on the drag motion such that, for example, the sensor is contacted first by a dry area to absorb excess fluid, then a soapy area to loosen remaining debris, then a second dry area to absorb the soap, then purified water to dilute the remaining soap, then third dry area to dry the sensor. Other arrangements can be made based on the cleaning needs.

Example Implementations

A particular group of applications involves blood (i.e., the sample 101 includes blood). The system can be used in detecting and analyzing types of cells in the blood, counting cells of various types in the blood, determining the normality of cells in the blood, monitoring the function of cells in the blood, and analyzing the chemistry of the blood.

Blood counts, in which cells or cellular elements of particular kinds such as white cells, red cells, and platelets, are counted in a carefully controlled volume of blood, are ubiquitous in the health care system in developed countries. Blood counts are highly useful in diagnosing pathologies and health conditions, determining their severity, and determining changes in such conditions over time. Over 250 million blood counts are done annually in the United States. A common form of blood count counts a variety of different elements in the blood and their properties and is known as a complete blood count (CBC).

Blood counts can be expensive and tend to be performed on expensive large dedicated machines operated in dedicated labs, for example, in hospitals or clinics. They are therefore not always available to poor or remote populations. This delivery model can also slow down the turn-around time and make the blood counts inconvenient to patients. Obtaining the amounts of blood generally needed for the counts carried out by such labs typically requires that the patient undergo venipuncture by a skilled technician; this procedure is often difficult, e.g., in pediatric or geriatric patients.

The system can be configured to define a small and precisely controlled sample space volume between a lid and the sensor surface.

Concentrating White Blood Cells

White blood cells (WBC) are at a relatively low concentration in blood, and the concentration can be further reduced by any dilution added to the blood in preparation of the sample. As a result the total number of white blood cells on the sensor surface to be imaged or counted can be low. Generally, the counting error for particles is the square root of the count, and a low number of particles to be counted may lead to a high percent error and standard error.

Figure 5A:
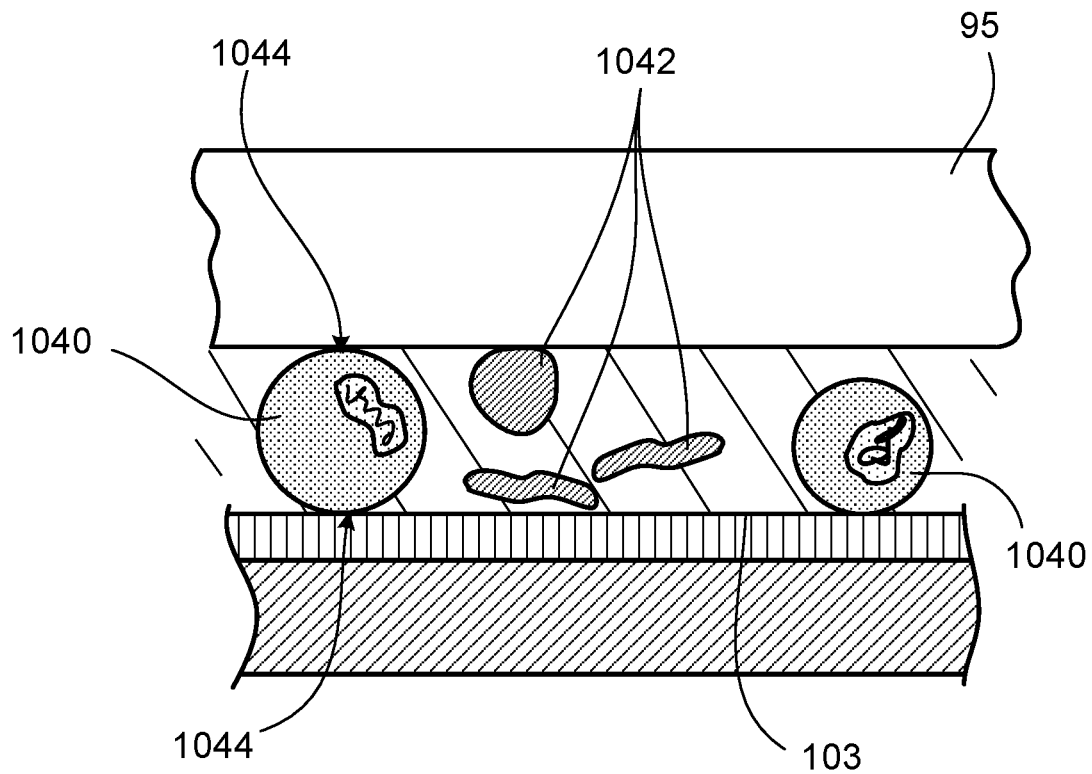
Figure 5B:
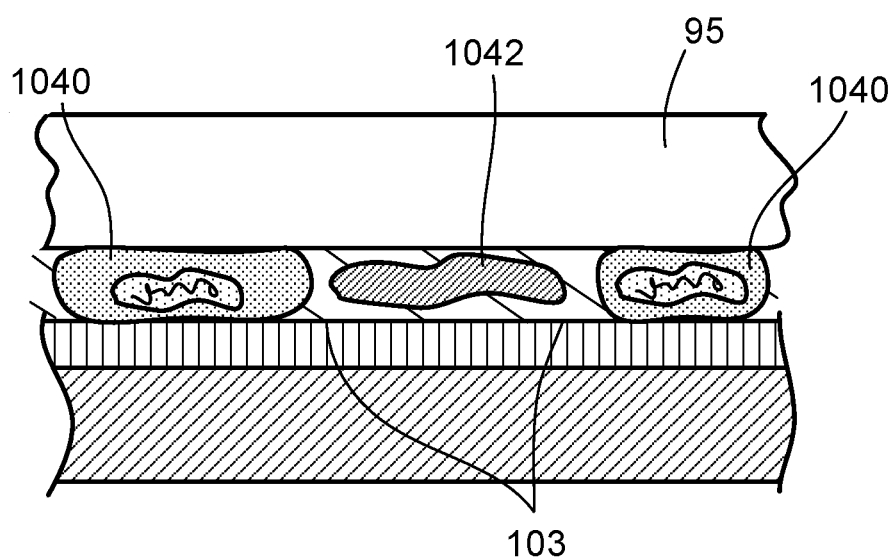

Referring to FIGS. 5A and 5B, the white blood cell concentration can be increased in a predictable manner. In some implementations, suitable spacer beads can be used such that an average concentration of red blood cells (RBC) 1042 can be maintained at a desired level on the sensor surface, while the while blood count is increased. Generally, as the chamber top 95 descends towards the sample, the cells that are in contact with the surface of the chamber top and the surface of the sensor at opposite directions (at contact points 1044) can be trapped. For example, when the cells are being compressed between the opposing surfaces, the cells generally do not move. Accordingly, the size of the spacer beads can be chosen such that the distance between the surfaces of the chamber top and the sensor is less than the average diameter of the white blood cells. In some situations, to maintain the concentration of the red blood cells, the beads can have a diameter larger than the average diameter of the red blood cells. The descent chamber top compresses the white blood cells having an average diameter or larger diameter without compressing the red blood cells having an average diameter or smaller diameter. As the total volume of the sample is reduced with the chamber top descending to reach the bead diameter, the concentration of the white blood cells on the sensor surface increases. An example of the bead diameter can be 7 microns. Other suitable diameters can be selected to control the concentration of different cell types in the sample.

Based on the height of the chamber during imaging (after the chamber top 95 completes its descent) and the surface area of the sensor that measures the cells, the volume of the white blood cells can be calculated. This volume can be used to determine the average diameter of the white blood cells, which is about the same as the chamber height measured at the moment the descending chamber top initially traps the white blood cells. Accordingly, the concentration of white blood cells can be increased in proportion to their size, relative to the concentration of smaller, untrapped cells, such as the red blood cells. The relationship between the size the concentration of the white blood cells is integrated over all the white blood cell sizes to obtain the average concentration (the bulk concentration in the sample before the cells are concentrated). More white blood cells are counted than expected by their initial concentration in the sample dispensed to the chamber, counting statistics can be improved.

Loading the Sensor

In some implementations, the sample is made ready for imaging in the chamber (or between the chamber top and the sensor) rapidly and in a reproducible manner. We sometimes call this process the sample filling process. The rapid process can prevent evaporation of the sample and reduce the resting time of the sample during which the sample units can redistribute within the fluid (e.g., by sedimentation due to gravitational forces).

In some implementations, before the sample is dispensed onto the sensor surface, the chamber top can be lowered to relatively close to the sensor surface, e.g., less than 1 mm from the sensor surface. After the sample is introduced under the chamber top, the sample fills the chamber via capillary forces. Once the chamber is sufficiently filled, the chamber top is lowered to prepare a desired amount of sample for imaging.

Figure 6A:
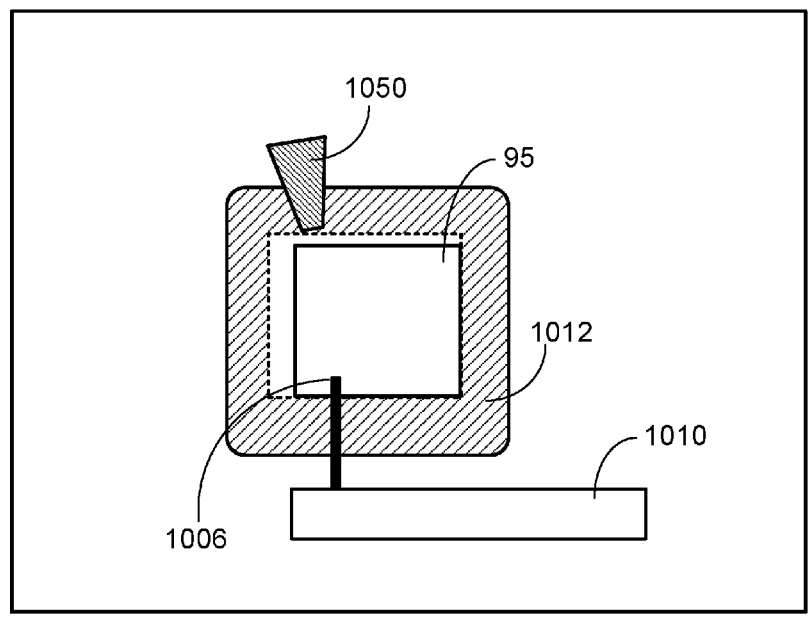
Figure 6B:
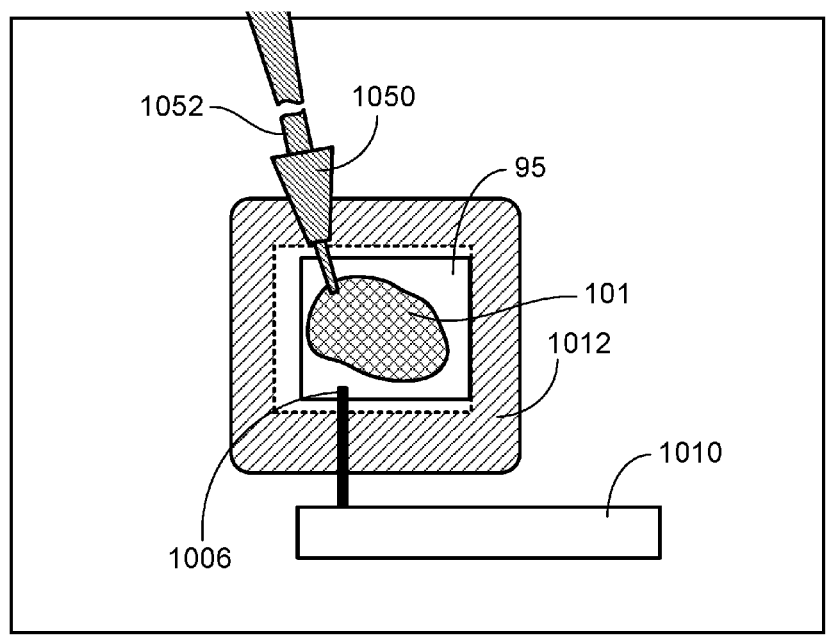
Figure 7:
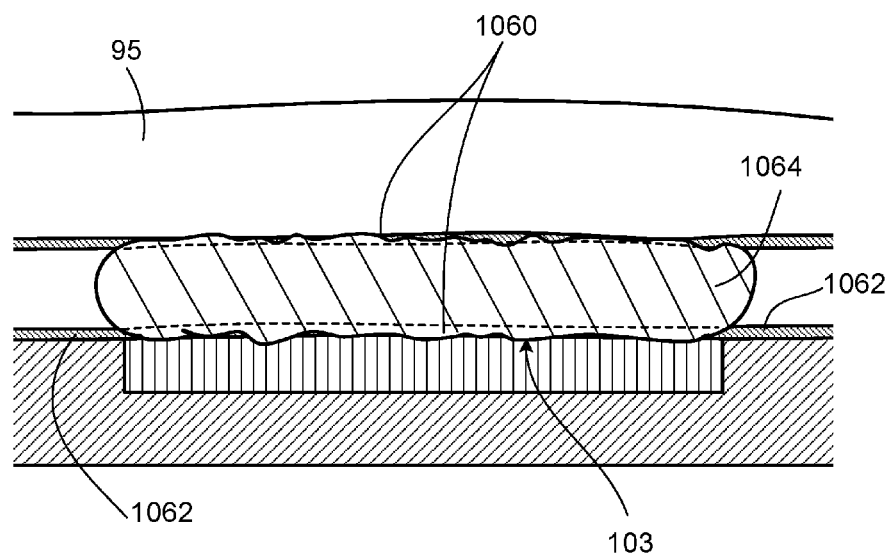

Referring to FIGS. 6A, 6B, and 7, a guide 1050 for the fluid-loading pipette tip 1052 is used to bring the tip 1052 close to the edge of the chamber top, so that the sample 101 is deposited at the same location on the sensor surface each time.

In some implementations, the chamber top and/or the image sensor surface is coated with hydrophilic coating(s) 1060 to enhance the capillary force and increase the speed of the sample filling process. Also, hydrophobic coatings 1062 can be used surrounding the sensor active area to contain the liquid specimen 1064.

In situations when settling of the sample units is an important concern, the sample can be mixed, e.g., during fluid ejection and/or chamber top descent, either or both of which can be automatically controlled, e.g., by pumps, actuators, etc.

Data Collection and Analysis

Figure 8:
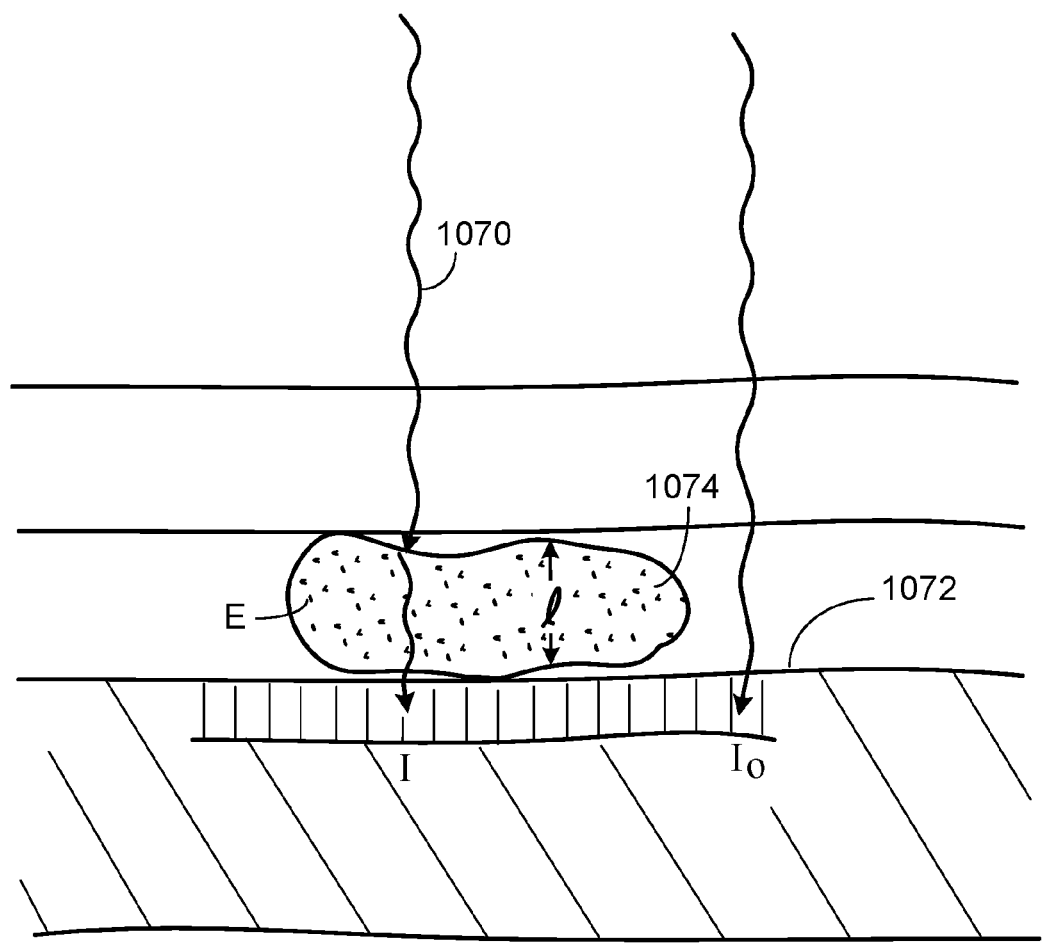
Figure 9:
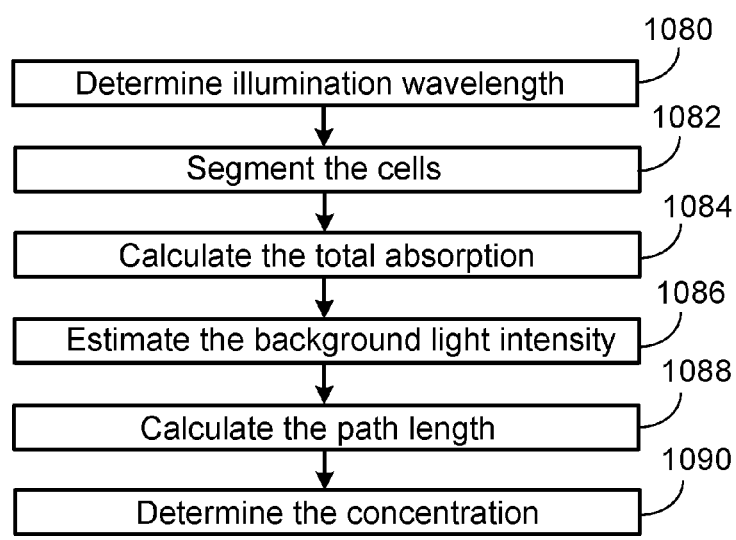
FIG. 9 is a flow diagram.

The data collected through the imaging process can be processed to produce various results of interest. As an example, a method for calculating the concentration of a light absorbing substance (or absorber) in any cell type, e.g., the hemoglobin content of individual red blood cells is described below in connection with FIGS. 8 and 9.

a) An illumination wavelength 1070 optimized for the absorber is determined (1080) for use. Generally, the wavelength for achieving high image contrast and high accuracy is the maximum absorption wavelength for the absorber.

b) The cells of the appropriate type is segmented 1082 via computer vision or by hand. The equation related to spectroscopy is Beer's law ($I/I_0 = e^{-\epsilon Cl}$), where I is the intensity after transmission through the sample (e.g., the red blood cell), $I_0$ is the intensity after transmission through water/non-absorbing material, c is the extinction coefficient of the substance (e.g., hemoglobin) at the illumination wavelength, C is the concentration of absorber, and l is the path length of light through the cell 1074.

c) The total absorption (I) is calculated 1084 by averaging the intensity of the pixels within the cell 1074.

d) The background light intensity ($I_0$) at the location of the RBC is estimated 1086, e.g., using a CV method (e.g., by identifying background regions 1072 near the cell 1074 and interpolating/extrapolating their values to where the cell is)

e) The path length (l) can be calculated 1088, e.g., using an analytical or statistical model or, if the sample is compressed, the chamber height.

f) The concentration of the absorber is therefore determined 1090 using the above formula.

Although the steps are presented in sequence in the description and FIG. 10, the actual data collection and analysis do not have to follow this example sequence and can be performed in any suitable sequence.

In some implementations, analytical or statistical models can be used to correct for deviations from Beer's law. The deviations may be caused by, e.g., uneven thickness (path length) across the cell, reflections off the cell wall, lensing that changes the path length of the light through the cell compared to the path length of the light travelling between two flat surfaces, light scattering (the sensor will record the signal from forward-scattered light as well as the transmitted light), and others.

In some implementations, the accuracy of the concentration may be enhanced using the average hemoglobin measurement by ignoring any cells that are near illumination defects and any cells that are bordering other cells.

In applying the hemoglobin measurement to blood samples, the illumination wavelength can be an isosbestic point of hemoglobin and oxyhemoglobin, since both species can occur in blood. Alternatively, the absorption maximum for oxyhemoglobin could be used as long as the blood has been adequately exposed to air during handling, converting all hemoglobin to oxyhemoglobin.

Alternatively, the maximum absorbing wavelength for carboxyhemoglobin or methehemoglibin can be used if it is desired to detect the presence of these molecules for diagnostic purposes. The maximum absorbing wavelength for carboxyhemoglobin or methehemoglibin can also be used to measure normal hemoglobin concentration if a methylating or carboxylating agent is included in the diluent to convert hemoglobin to carboxyhemoglobin or methehemoglibin.

A wide range of products can be manufactured and delivered based on the architecture and principles that we have discussed. The products could include sensor units, sensor units plus readout units, sensor units plus headboards, sample chambers, chamber tops (or lids), sensor units plus pipettes, sensor units plus pumps, system devices, handheld devices, plugins and attachments to other equipment, pipettes, preloaded pipettes, image processors, software, light sources, sample chambers plus light sources plus sensors plus headboards plus electronics in complete devices, and combinations of two or more of these as well as other components.

In considering the wide range of operations performed by the sensors and systems and the broad spectrum of applications, it may be useful to recognize that some relate to imaging, some to analysis, and some to a combination of analysis and imaging.

Other embodiments are within the scope of the following claims and other claims.

What is claimed is:

1. An apparatus comprising
a two-dimensional arrangement of light sensitive elements exposed at a sensor surface of an imaging sensor,
a second surface to be moved into a predefined position relative to the imaging surface to form a sample space that is between the sensor surface and the second surface and contains at least part of a sample, and
a mechanism configured to cause mixing of the sample by moving the second surface toward and away from the sensor surface repeatedly.

2. The apparatus of claim 1 in which the mechanism moves the second surface at a controlled velocity.

3. The apparatus of claim 1 in which the mechanism comprises an actuator.

4. The apparatus of claim 3 in which the actuator comprises a pump.

5. The apparatus of claim 1 in which the mechanism is configured to move the second surface toward and away from the sensor surface without reaching the predefined position.

6. The apparatus of claim 1 in which the mixing of the sample comprises causing sample units to be evenly distributed in the sample.

7. The apparatus of claim 1 in which the mechanism is automatically controlled.

8. The apparatus of claim 1 in which the mechanism is configured to move the second surface along a trajectory.

9. The apparatus of claim 1 in which the trajectory comprises an arc.

10. The apparatus of claim 1 in which the sample comprises elements that are to be counted, and the mechanism is configured so that the moving of the second surface causes the elements to be evenly distributed across the sensor surface and causes the bulk concentration of the elements in the sample after the second surface reaches the predefined position to be consistently proportional to the bulk concentration of the elements in the sample when the second surface is in an initial position.

11. The apparatus of claim 1 in which the bulk concentration of elements in the sample after the second surface reaches the predefined position is the same as or higher than the bulk concentration of the elements in the sample when the second surface is in an initial position.

12. The apparatus of claim 1 in which the second surface has an alignment edge that bears against an alignment edge associated with the sensor surface to define a pivot axis about which the second surface is to be rotated to reach the predefined position.

13. A method comprising
repeatedly moving a first surface toward and away from a sensor surface of an imaging sensor, then moving the first surface to a predetermined position relative to the sensor surface, and using the imaging sensor to capture an image of a sample in a space between the first surface and the sensor surface when the first surface is at the predetermined position.

14. The method of claim 13 comprising providing the sample in a space between the first surface and the second surface before the imaging sensor captures the image.

15. The method of claim 14 in which providing the sample comprises enabling capillary flow to move into the sample into the space.

16. The method of claim 13 in which moving the first surface to the predetermined position relative to the sensor surface comprises forcing the sample against the sensor surface.

17. The method of claim 13 in which at least one of the repeated moving or the moving of the first surface to the predetermined position is controlled automatically.

18. The method of claim 13 comprising ejecting the sample into the space before repeatedly moving the first surface toward and away from the sensor surface.

19. The method of claim 18 in which the sample is ejected automatically.

* * * * *